United States Patent
Farokhzad et al.

(10) Patent No.: US 10,314,917 B2
(45) Date of Patent: Jun. 11, 2019

(54) TARGETED POLYMERIC INFLAMMATION-RESOLVING NANOPARTICLES

(71) Applicants: The Brigham and Women's Hospital, Inc., Boston, MA (US); Massachusetts Institute of Technology, Cambridge, MA (US); The Trustees of Columbia University in the City of New York, New York, NY (US)

(72) Inventors: Omid C. Farokhzad, Waban, MA (US); Xueqing Zhang, Cambridge, MA (US); Xiaoyang Xu, Cambridge, MA (US); Nazila Kamaly, Boston, MA (US); Mingming Ma, Boston, MA (US); Pedro M. Valencia, Miami, FL (US); Robert S. Langer, Newton, MA (US); Ira Tabas, New York, NY (US); Gabrielle Beth Fredman, New York, NY (US)

(73) Assignees: The Brigham and Women's Hospital, Inc., Boston, MA (US); Massachusetts Institute of Technology, Cambridge, MA (US); The Trustees of Columbia University in the City of New york, New York, NY (US)

( * ) Notice: Subject to any disclaimer, the term of this patent is extended or adjusted under 35 U.S.C. 154(b) by 200 days.

(21) Appl. No.: 14/777,304

(22) PCT Filed: Mar. 17, 2014

(86) PCT No.: PCT/US2014/030563
§ 371 (c)(1),
(2) Date: Sep. 15, 2015

(87) PCT Pub. No.: WO2014/145749
PCT Pub. Date: Sep. 18, 2014

(65) Prior Publication Data
US 2016/0022835 A1    Jan. 28, 2016

Related U.S. Application Data

(60) Provisional application No. 61/799,171, filed on Mar. 15, 2014.

(51) Int. Cl.
| | |
|---|---|
| A61K 38/16 | (2006.01) |
| A61K 47/48 | (2006.01) |
| A61K 9/51 | (2006.01) |
| A61K 31/195 | (2006.01) |
| A61K 47/60 | (2017.01) |
| A61K 47/54 | (2017.01) |
| A61K 47/59 | (2017.01) |
| A61K 47/64 | (2017.01) |
| A61K 47/69 | (2017.01) |

(52) U.S. Cl.
CPC ...... *A61K 47/48915* (2013.01); *A61K 9/5153* (2013.01); *A61K 31/195* (2013.01); *A61K 38/16* (2013.01); *A61K 47/544* (2017.08); *A61K 47/593* (2017.08); *A61K 47/60* (2017.08); *A61K 47/64* (2017.08); *A61K 47/6937* (2017.08)

(58) Field of Classification Search
CPC ............................................... A61K 47/48915
See application file for complete search history.

(56) References Cited

U.S. PATENT DOCUMENTS

| | | | |
|---|---|---|---|
| 6,586,403 | B1 | 7/2003 | Mathison et al. |
| 6,852,697 | B1 | 2/2005 | Mathison et al. |
| 7,094,760 | B2 | 8/2006 | Mathison et al. |
| 7,153,835 | B2 | 12/2006 | Mathison |
| 8,349,801 | B2 | 1/2013 | Cohen et al. |
| 2004/0022843 | A1 | 2/2004 | Singh et al. |

(Continued)

FOREIGN PATENT DOCUMENTS

| | | |
|---|---|---|
| WO | 98006742 | 2/1998 |
| WO | WO 98/006742 | 2/1998 |

(Continued)

OTHER PUBLICATIONS

Chuu et al. (AntiCaner Resarch. 2010; 30:3643-3648).*
Bandeira-Melo et al. (The Journal of Pharmacology and Experimental Therapeutics. 2005; 313(3): 1416-1422).*
Lux et al. (J. Am. Chem. Soc. 2012; 134: 15758-15764).*
Ekerljung et al. (Biochemical and Biophysical Research Communications. Dec. 12, 2008; 377(12): 489-494) (Year: 2008).*
Spagnoli et al. J Nucl Med, Nov. 2007; 48(11): 1800-1815 (Year: 2007).*
Peters et al. PNAS. Jun. 16, 2009. 106(24): 9815-9819 (Year: 2009).*

(Continued)

*Primary Examiner* — Scott Long
(74) *Attorney, Agent, or Firm* — Pabst Patent Group LLP

(57) ABSTRACT

Sub-100 micron multimodal nanoparticles have four main components: 1) a target element (peptides, lipids, antibodies, small molecules, etc.) that can selectively bind to cells, tissues, or organs of the body; 2) a diagnostic agent such as a fluorophore or NMR contrast agent that allows visualization of nanoparticles at the site of delivery and/or a therapeutic or prophylactic agent; 3) an outside "stealth" layer that allows the particles to evade recognition by immune system components and increase particle circulation half-life; and 4) a biodegradable polymeric material, forming an inner core which can carry therapeutics and release the payloads at a sustained rate after systemic, intraperitoneal, or mucosal administration. These particles possess excellent stability, high loading efficiency, multiple agent encapsulation, targeting and imaging. They are targeted to sites of, or associated with, inflammation caused by a disease, disorder; trauma, chemotherapy or radiation.

20 Claims, 8 Drawing Sheets
Specification includes a Sequence Listing.

(56) References Cited

U.S. PATENT DOCUMENTS

| | | | | |
|---|---|---|---|---|
| 2009/0074828 A1* | 3/2009 | Alexis | ................ | A61K 9/5123 424/422 |
| 2010/0120891 A1 | 5/2010 | Camby et al. | | |
| 2011/0143993 A1* | 6/2011 | Langer | .................... | B82Y 5/00 514/1.4 |
| 2013/0028857 A1* | 1/2013 | Gao | .................... | A61K 39/385 424/78.29 |

FOREIGN PATENT DOCUMENTS

| WO | 03066670 | 7/2003 |
|---|---|---|
| WO | WO 03/066670 | 7/2003 |

OTHER PUBLICATIONS

Franchimont et al. Regulatory Peptides. 1998; 73: 59-65 (Year: 1998).*

Perretti et al. Nature Reviews Immunology vol. 9, pp. 62-70 (2009) (Year: 2009).*

Amulic, et al., "Neutrophil function: from mechanisms to disease", *Annu, Rev. Immunol.*, 30:459-89 (2012).

Bandeira-Melo, et al., "A novel effect for annexin 1-derived peptide ac2-26: reduction of allergic inflammation in the rat", *J Pharmacol Exp Ther.*, 313(3):1416-22 (2005).

Bannenberg, et al., "Molecular circuits of resolution: formation and actions of resolvins and protectins", *J Immunol.*, 174(7):4345-55 (2005).

Calkin, et al., "Liver x receptor signaling pathways and atherosclerosis", *Arterioscler Thromb Vasc Biol.*, 30(8):1513-8 (2010).

Chan, et al., "Polymeric nanoparticles for drug delivery", *Methods Mol Biol.*, 624:163-75(2010a).

Chan, et al., "Spatiotemporal controlled delivery of nanoparticles to injured vasculature", *PNAS*, 107(5):2213-8 (2010b).

Chiang, et at, "Anesthetics impact the resolution of inflammation", *PLoS One*, 3(4):e1879 (2008).

Dufton, et al., "Anti-inflammatory role of the murine formyl-peptide receptor 2: ligand-specific effects on leukocyte responses and experimental inflammation", *J Immunol.*, 184(5):2611-9 (2010).

Facio, et al., "Annexin 1 mimetic peptide protects against renal ischemia/reperfusion injury in rats", *J Mol Med (Berl).*, 89(1):51-63 (2011).

Fadok, et al., "Exposure of phosphatidylserine on the surface of apoptotic lymphocytes triggers specific recognition and removal by macrophages", *J Immunol.*, 148(7):2207-16 (1992).

Farokhzad, et al., "Nanoparticle-aptamer bioconjugates: a new approach for targeting prostate cancer cells", *Cancer Res.*, 64(21):7668-72 (in eng) (2004).

Farokhzad, et al., "Targeted nanoparticle-aptamer bioconjugates for cancer chemotherapy in vivo", *PNAS*, 103(16):6315-20 (2006).

Farokhzad, "Nanotechnology for drug delivery: the perfect partnership", *Expert Opin Drug Deliv.*, 5(9):927-9 (2008).

Feig, et al., "LXR promotes the maximal egress of monocyte-derived cells from mouse aortic plaques during atherosclerosis regression", *J Clin Invest.*, 120(12):4415-24).

Fredman, et al., "Self-limited versus delayed resolution of acute inflammation: temporal regulation of pro-resolving mediators and microRNA", *Sci Rep.*, 2:639 (2012).

Gu, et al., "Precise engineering of targeted nanoparticles by using self-assembled biointegrated block copolymers", *PNAS*, 105(7):2586-91 (2008).

Hamzah, et al., "Specific penetration and accumulation of a homing peptide within atherosclerotic plaques of apolipoprotein E-deficient mice", *PNAS*, 108(17):7154-9 (2011).

Hansson, "Inflammation, atherosclerosis, and coronary artery disease", *N Eng J Med* 352(16):1685-95 (2005).

Harel-Adar, et al., "Modulation of cardiac macrophages by phosphatidylserine-presenting liposomes improves infarct repair", *PNAS,*, 108(5):1827-32 (2011).

Hrkach,et al., "Preclinical development and clinical translation of a PSMA-targeted docetaxel nanoparticle with a differentiated pharmacological profile", *Sci Transl Med.*, 4(128):128ra139 (2012).

Joseph, et al., "Direct and indirect mechanisms for regulation of fatty acid synthase gene expression by liver X receptors", *J Biol Chem.*, 277(13):11019-25 (2002a).

Joseph, et al., "Synthetic LXR ligand inhibits the development of atherosclerosis in mice", *PNAS*, 99(11):7604-7609 (2002b).

Kalluri, "Basement membranes: structure, assembly and role in tumour angiogenesis", *Nature reviews. Cancer*, 3(6):422-33 (2003).

Kamaly, et al., "Targeted polymeric therapeutic nanoparticles: design, development and clinical translation", *Chem Soc Rev.*, 41(7):2971-3010 (2012).

La, et al., "Annexin 1 peptides protect against experimental myocardial ischemia-reperfusion: analysis of their mechanism of action", *FASEB J*, 15(12):2247-56 (2001).

Lawrence and Gilroy, "Chronic inflammation: a failure of resolution", *Int. J. Exp. Pathol.*, 88:85-94 (2007).

Levin, et al., "Macrophage liver X receptor is required for antiatherogenic activity of LXR agonists", *Arterioscler Thromb Vasc Biol.*, 25(1):135-42 (2005).

Levy, et al., "Lipid mediator class switching during acute inflammation: signals in resolution" *Nat Immunol.*, 2(7):612-9 (2001).

Libby, et al., "Progress and challenges in translating the biology of atherosclerosis" *Nature*, 473(7347):317-25 (2011).

Libby, "Inflammation in atherosclerosis", *Nature*, 420(6917):868-74 (2002).

Makadia, et al., "Poly Lactic-co-Glycolic Acid (PLGA) as Biodegradable Controlled Drug Delivery Carrier", *Polymers (Basel).*, 3(3):1377-97 (2011).

Medzhitov, "Inflammation 2010: new adventures of an old flame", *Cell*, 140:771-6 (2010).

Mora-Huertas, et al., "Polymer-based nanocapsules for drug delivery", *Int J Pharm.*, 385(1-2):113-42 (2010).

Navarro-Xavier, et al., "A new strategy for the identification of novel molecules with targeted proresolution of inflammation properties", *J Immunol.*, 184(3):1516-25 (2010).

Nathan and Ding, "Nonresolving inflammation", *Cell*, 140:871-82 (2010).

Norling, et al., "Cutting edge: Humanized nano-proresolving medicines mimic inflammation-resolution and enhance wound healing", *J Immunol.*, 186(10):5543-7 (2011).

Peer, et al., "Nanocarriers as an emerging platform for cancer therapy", *Nat Nanotechnol.*, 2(12):751-60 (2007).

Perretti and Dalli, "Exploiting the Annexin A1 pathway for the development of novel anti-inflammatory therapeutics", *Br J Pharmacol.*, 158(4):936-46 (2009).

Perretti, et al., "Involvement of the receptor for formylated peptides in the in vivo anti-migratory actions of annexin 1 and its mimetics", *Am J Pathol.*, 158(6):1969-73 (2001).

Perretti, et al., "Endogenous lipid- and peptide-derived anti-inflammatory pathways generated with glucocorticoid and aspirin treatment activate the lipoxin A4 receptor", *Nat Med.*, 8(11):1296-1302 (2002).

Perretti, et al., "Annexin A1 and glucocorticoids as effectors of the resolution of inflammation", *Nat Rev Immunol.*, 9(1):62-70 (2009b).

Peters, et al., "Targeting atherosclerosis by using modular, multifunctional micelles", *PNAS*, 106(24):9815-9 (2009).

Qiu, et al., "IMP and AMP deaminase in reperfusion injury downregulates neutrophil recruitment", *PNAS*, 97(8):4267-72 (2000).

Quintanar-Guerrero, et al., "Preparation techniques and mechanisms of formation of biodegradable nanoparticles from preformed polymers", *Drug Dev Ind Pharm.*, 24(12):1113-28 (1998).

Rius, et al., "Resolvin D1 primes the resolution process initiated by calorie restriction in obesity-induced steatohepatitis", *FASEB J.*, 28(2):836-48 (2014).

Samstein, et al., "The use of deoxycholic acid to enhance the oral bioavailability of biodegradable nanoparticles", *Biomaterials*, 29(6):703-8 (2008).

Schultz, et al., "Role of LXRs in control of lipogenesis", *Genes Dev.*, 14(22):2831-8 (2000).

Schwab, et al., Resolvin E1 and protectin D1 activate inflammation-resolution programmes, *Nature*, 447(4176):869-74 (2007).

(56) References Cited

OTHER PUBLICATIONS

Serhan, et al., "Resolving inflammation: dual anti-inflammatory and pro-resolution lipid mediators", *Nat Rev Immunol.*, 8(5):349-61 (2008).

Serhan, et al., "Resolution of inflammation: state of the art, definitions and terms", *FASEB J.*, 21(2)325-32 (2007).

Tabas, "Macrophage death and defective inflammation resolution in atherosclerosis", *Nat Rev Immunol.*, 10(1):36-46 (2010).

Tangirala, et al., "Identification of macrophage liver X receptors as inhibitors of atherosclerosis", *PNAS*, 99(18):11896-901 (2002).

Yoshikawa, et al., "Identification of liver X receptor-retinoid X receptor as an activator of the sterol regulatory element-binding protein 1c gene promoter", *Mol Cell Biol.*, 21(9):2991-3000 (2001).

Zwaal, et al., "Surface exposure of phosphatidylserine in pathological cells", *CMLS, Cell. Mol. Life Sci.*, 62:971-88 (2005).

Chiang, et al., "Anesthetics impact the resolution of inflammation", PLoS One, 3 (4):e1879 (2008).

Facio, et al., "Annexin 1 mimetic peptide protects against renal ischemla/reperfusion injury in rats", J Mol Med (Berl)., 89(1):51-63 (2011).

Feig, et al., "LXR promotes the maximal egress of monocyte-derived cells from mouse aortic plaques during atherosclerosis regression", J Clin Invest., 120 (12):4415-24 (2010).

Hansson, "Inflammation, atherosclerosis,, and coronary artery disease", N Engl J Med 352(16):1685-95 (2005).

Hrkach, et al., "Preclinical development and clinical translation of a PSMA-targeted docetaxel nanoparticie with a differentiated pharmacological profile", Sci Transl Med., 4 (128):128ra139 (2012).

Kamaly, "Targeted polymeric therapeutic nanoparticles: design, development and clinical translation", Chem Soc Rev., 41(7):2971-3010 (2012).

Levin, et al., "Madrophage liver X receptor is required for antiatherogenic activity of LXR agonists", Arterioscler Thromb Vasc Biol., 25(1):135-42 (2005).

Perretti, et al., "Endogenous lipid- and peptide-derived anti-inflammatory pathways with glucocorticoid and aspirin treatment activate the lipoxin A4 receptor", Nat Med., 8(11):1296-1302 (2002).

International Search Report for PCT application PCT/US2014/030563 dated Aug. 20, 2014.

\* cited by examiner

Ac2-26 NP

Ac2-26 + Col IV NP

Scrm-Ac2-26 NPs

Scrm-Ac2-26 + Col IV NP $\sim\!\!\sim\!\!\sim\!\!\sim$ PLGA$_{43.5k}$PEG$_{3.4k}$COOH $\sim\!\!\sim\!\bullet$ PLGA$_{43.5k}$ Alexa 647

$\sim\!\!\sim\!\!\sim\!\!\blacktriangleleft$ PLGA$_{43.5k}$ PEG$_{3.4k}$Col IV $\sim\!\sim$ Ac2-26 peptide     $\sim\!\!\sim$ Scrm-Ac2-26 peptide

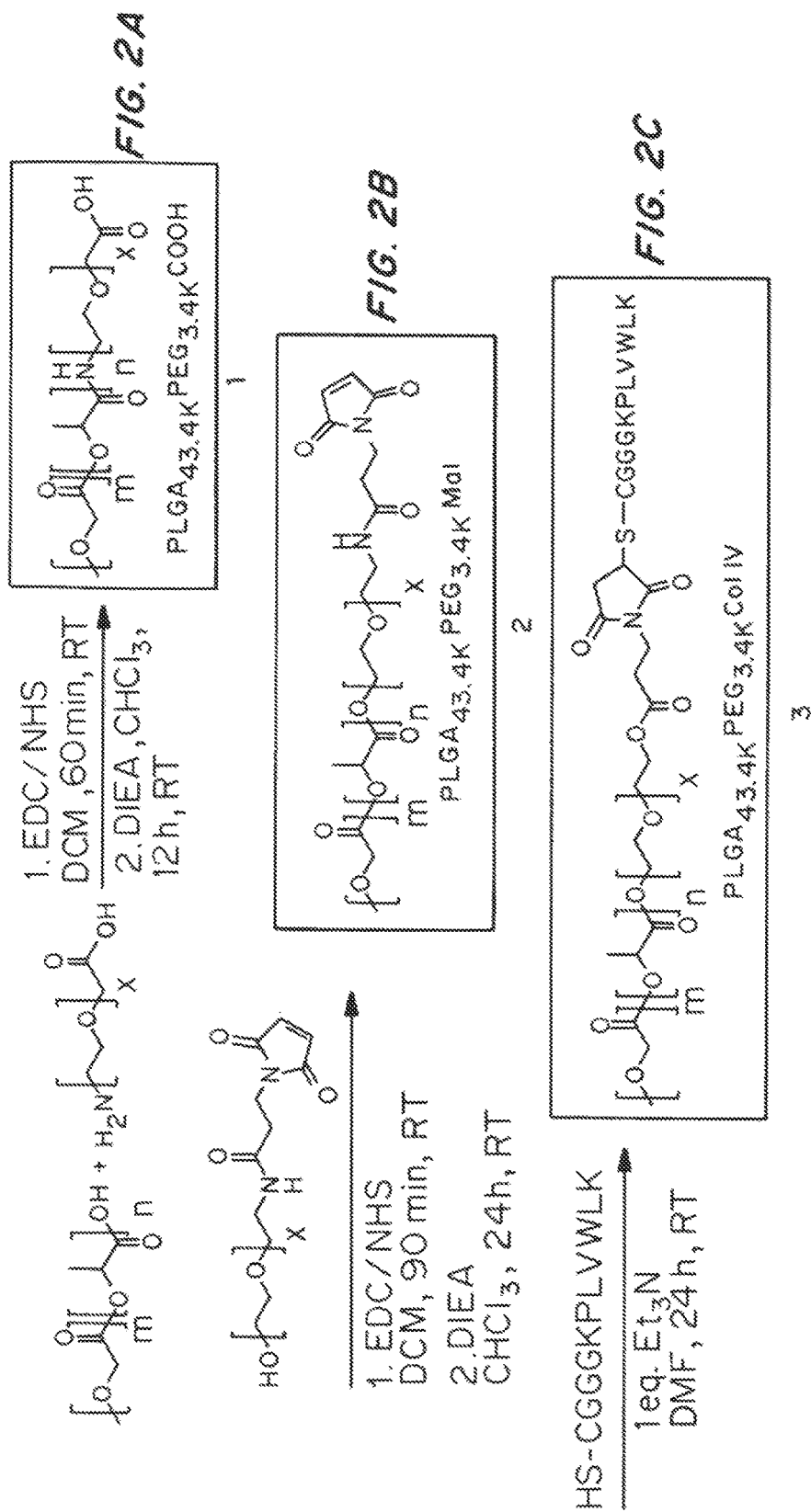

SEQUENCE LISTING

<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Peptide

<400> SEQUENCE: 1

Cys Arg Glu Lys Ala
1               5

<210> SEQ ID NO 2
<211> LENGTH: 9
<212> TYPE: PRT
<213> ORGANISM: Artificial Sequence
<220> FEATURE:
<223> OTHER INFORMATION: Peptide

<400> SEQUENCE: 2

Cys Arg Lys Arg Leu Asp Arg Asn Cys
1               5

<210> SEQ ID NO 3
<211> LENGTH: 11
<212> TYPE: PRT
<213> ORGANISM: Artificial Sequence
<220> FEATURE:
<223> OTHER INFORMATION: Peptide

<400> SEQUENCE: 3

Lys Leu Trp Val Leu Pro Lys Gly Gly Gly Cys
1               5                   10

<210> SEQ ID NO 4
<211> LENGTH: 25
<212> TYPE: PRT
<213> ORGANISM: Artificial Sequence
<220> FEATURE:
<223> OTHER INFORMATION: Peptide

<400> SEQUENCE: 4

Glu Gln Trp Tyr Gln Asn Thr Glu Glu Val Ser Ala Ala Phe Gln Lys
1               5                   10                  15

Val Val Lys Glu Glu Met Ile Phe Leu
            20                  25

<210> SEQ ID NO 5
<211> LENGTH: 7
<212> TYPE: PRT
<213> ORGANISM: Artificial Sequence
<220> FEATURE:
<223> OTHER INFORMATION: Peptide

<400> SEQUENCE: 5

Lys Leu Trp Val Leu Pro Lys
1               5

<210> SEQ ID NO 6
<211> LENGTH: 4
<212> TYPE: PRT
<213> ORGANISM: Artificial Sequence
<220> FEATURE:
<223> OTHER INFORMATION: Peptide

<400> SEQUENCE: 6

Gly Gly Gly Cys
1

TARGETED POLYMERIC INFLAMMATION-RESOLVING NANOPARTICLES

CROSS-REFERENCE TO RELATED APPLICATIONS

This application is a 371 application of International Application No. PCT/US2014/030563, which claims benefit and priority to U.S. Ser. No. 61/799,171, entitled "Targeted Polymeric Inflammation Resolving Nanoparticles" to Omid C. Farokhzad, Xueqing Zhang, Xiaoyang Xu, Nazila Kamaly, Mingming Ma, Pedro M. Valencia, Robert S. Langer, Ira Tabas and Gabrielle Beth Fredman, filed Mar. 15, 2013, all of which are incorporated herein by reference.

REFERENCE TO SEQUENCE LISTING

The Sequence Listing submitted as a text file named "BWH_22007_21889_PCT_ST25," created on Mar. 17, 2014, and having a size of 1,538 bytes is hereby incorporated by reference.

STATEMENT REGARDING FEDERALLY SPONSORED RESEARCH OR DEVELOPMENT

This invention was made with support from: Contract HHSN268201000045C, from the National Heart, Lung, and Blood Institute, National Institutes of Health and NIH-NHLBI NO1 HV-08236 to Zahi Fayed and Robert Langer.

FIELD OF THE INVENTION

The present application is generally in the field of targeted polymeric nanoparticles which inhibit the inflammatory response, specifically Sub-100 micron multimodal nanoparticles which have four main components: 1) a targeting element that can selectively bind to cells, tissues, or organs of the body; 2) a diagnostic agent such as a fluorophore or NMR contrast agent that allows visualization of nanoparticles at the site of delivery and/or a therapeutic or prophylactic agent; 3) an outside "stealth" layer that allows the particles to evade recognition by immune system components and increase particle circulation half-life; and 4) a biodegradable polymeric material, forming an inner core which can carry therapeutics or other diagnostics.

BACKGROUND OF THE INVENTION

Acute inflammation is a protective response that combats invading organisms and repairs tissue injury (Majno & kris, *Cells, tissues, and disease: principles of general pathology* (Oxford University Press, New York) 2nd Ed pp xxviii, 1005 (2004)). Ideally this response is self-limited and leads to clearance of pathogens, cellular debris and inflammatory mediators, and allows tissues to return to homeostasis (Majno and Medzhitov, *Cell* 140:771-776 (2010)). However, an excessive inflammatory response impairs resolution and leads to chronic inflammation and subsequent tissue damage (Majno, et al. *FASEB J* 21(2):325-332 (2007); Lawrence & Gilroy, *Int. J. Exp. Pathol.* 88:85-94(2007). Increasing evidence suggests that excessive inflammation and impaired resolution play central roles in several prevalent diseases including cardiovascular, metabolic, and neurodegenerative diseases (Nathan & Ding, *Cell* 140:871-882 (2010)). Hence, development of therapeutics that temper inflammation and enhance resolution are of considerable interest.

Advances in vascular biology have revealed a pivotal role of inflammation in the pathophysiology of atherosclerosis, the major cause of cardiovascular diseases and the leading cause of morbidity and mortality in developed world (Hansson, *N Engl J Med* 352(16):1685-1695 (2005); Libby et al *Nature* 473(7347):317-325 (2011)). Atherosclerotic plaques develop through a maladaptive, macrophage-driven, chronic inflammatory response to subendothelial lipoproteins with defective inflammation resolution (Tabas, *Nat Rev Immunol* 10(1):36-46 (2010)). This defective resolution of inflammation results in an increased permeation of lipoproteins and adhesion molecules, followed by the recruitment of monocytes that differentiate into macrophages and eventually transform into lipid-laden foam cells beneath the endothelium. Through apoptosis and failure of efferocytosis, which is a specific and important component of the resolution response, these foam cells undergo secondary necrosis, leading to the formation of the necrotic core in atherosclerotic lesions. This atherogenic inflammatory cycle promotes the progression of atherosclerotic lesions into dangerous plaques that are vulnerable to rupture, which can in turn trigger acute, obstructive vascular thrombosis, myocardial infarctions, and most strokes (Libby, *Nature* 420(6917):868-874 (2002)). The knowledge of inflammatory cascade involved offers new opportunities for the treatment and prevention of atherosclerosis, among which nanoparticles (NPs) containing anti-inflammatory and pro-resolving agents present an attractive nanomedicine approach.

Atherosclerotic plaques develop through a maladaptive, macrophage-driven chronic inflammatory response to subendothelial lipoproteins. Macrophages are a key cell type in this inflammatory response and thus have thus emerged as a key imaging and therapeutic target for atherosclerosis.

Although a number of promising arterial-wall targets have been identified and validated using molecular-genetic approaches in animal models of atherosclerosis, many of these are not amenable to systemic or oral delivery due to the nature of the compounds (e.g., proteins), lack of efficient delivery to plaques, safety concerns related to delivery to the liver and other sites; pharmacokinetic issues (e.g. rapid drug clearance).

Resolution of inflammation is now considered to be a distinct process from anti-inflammatory processes. This is because in addition to serving as agonists to stop and lower neutrophil infiltration to inflamed tissues, pro-resolution molecules promote uptake and clearance of apoptotic cells as well as microbes by macrophages in inflamed sites' Resolution is accompanied by an active switch in the mediators that predominate in exudates. The initial mediators generated include prostaglandins and leukotrienes. Next, prostaglandin E2 and D2 gradually induce the production of mediators that have both anti-inflammatory and pro-resolution activities (collectively, pro-resolving lipid mediators (SPMs) such as lipoxions, resolvins, and protectins (reviewed in Serhan, et al *Nat Rev Immunol* 8(5):349-361 (2008)). Other examples of SPMs include maresins, and specific peptide mediators such as annexin A1 (Serhan, et al. *Nat Rev Immunol* 9(1):62-70 (2009)). These families of endogenous pro-resolution molecules are not immunosuppressive, but instead, function in resolution by activating specific mechanisms to promote homeostatis Serhan, et al *Nat Rev Immunol* 8(5):349-361 (2008)).

Bannenberg et al introduced and defined quantitative resolution indices in vivo that allow for temporal regulation of leukocyte trafficking and chemical mediators within inflammatory exudates (Bannenberg, et al. *J Immunol* 174(7):4345-4355 (2005)). These indices are the maximal neutrophil numbers that are present in the exudates ($\psi_{max}$); the time when $\psi_{max}$ occurs ($T_{max}$); and the resolution interval from $T_{max}$ to $T_{50}$ ($R_i$), i.e., the time it takes for the number of poly-morphonuclear neutrophils (PMNs) to reach half $\psi_{max}$. Importantly, these indices not only provide a quantitative measure of the specific actions of endogenous SPMs and peptides but also provide a means to investigate whether pharmacologic agents can enhance or impair resolution (Bannenberg, et al. *Nature* 447(7146):869-874 (2007)). In this regard, only a few widely used therapeutics have been assessed for their impact in programmed resolution (Schwab, et al. *J Immunol* 184(3):1516-1525 (2010)).

The resolution of inflammation is a highly complex process that can involve a balance of pro- and anti-inflammatory mediators (Serhan 2008; Bannenberg et al. *J Immunol* 174(7):4345-4355 (2005); Fredman, et al *Sci Rep* 2:639 (2012)). Therapeutics can impair or enhance resolution. For example, cyoclooxygenase and lipoxygenase inhibitors (Schwab, et al., *Nature*, 447(4176):869-74 (2007)) and lidocaine (Chiang, et al. *PLoS One* 3(4):e1879 (2008)) impair resolution. Most notable resolution "toxic" drugs are the COX-2 inhibitors that can block the production of $PGE_2$ and $PGD_2$, two critical mediators which initiate resolution (Levy, et al., *Nat Immunol* 2(7):612-619 (2001)). Aspirin and glucoroticoids can enhance resolution via the generation of aspirin-triggered SPMs (Serhan 2007) or by the endogenous production of annexin-A1, respectively (Perretti & Dalli, *Br J Pharmacol* 158(4):936-946 (2009)). SPMs and annexin-A1 can bind specific receptors and serve as agonists that trigger protective mechanisms and promote the return to homeostasis (Perretti 2009; Serhan 2008). An ideal therapeutic is one that tempers excessive inflammation and enhances resolution.

Many diseases and disorders involve inflammation. Inflammation may be beneficial, in the case of infection, or damaging, as in cardiovascular disorders, autoimmune disorders, scarring, allergic reactions, chronic lung disorders, ischemia (stroke, traumatic brain injury), to name only a few.

It is therefore an object of the present invention to provide a method and compositions for treatment inflammation.

It is a further object of the present invention to provide a method and compositions for more selective treatment of inflammation, including cardiovascular or ischemic inflammatory disorders.

SUMMARY OF THE INVENTION

Sub-100 micron multimodal nanoparticles are provided, which have four main components: 1) a targeting element (peptides, lipids, antibodies, small molecules, etc.) that can selectively bind to cells, tissues, or organs of the body; 2) a diagnostic agent such as a fluorophore or NMR contrast agent that allows visualization of nanoparticles at the site of delivery and/or a therapeutic or prophylactic agent; 3) an outside "stealth" layer that allows the particles to evade recognition by immune system components and increase particle circulation half-life; and 4) a biodegradable polymeric material, forming an inner core which can carry therapeutics and release the payloads at a sustained rate after systemic, intraperitoneal, or mucosal administration.

Preferred polymers are can be one or more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide, collectively referred to herein as "PLA", and copolymers of polyethylene glycol (PEG) and the polyesters, such as various forms of PLGA-PEG or PLA-PEG copolymers, collectively referred to herein as "PEGylated polymers". The PEG region can be covalently associated with polymer to yield "PEGylated polymers".

In some embodiments, the nanoparticles contain a targeting moiety conjugated to the polymer of the nanoparticle, in a weight ratio of non-functionalized polymers, for example, a polymer/polymer-peptide weight ratio of up to 39. Examples of targeting moieties include collagen IV, CREKA (SEQ ID NO: 1), LyP-I, CRKRLDRNC (SEQ ID NO: 2), or their combinations at various molar ratios. In some embodiments, the nanoparticles include targeting moieties that selectively bind inflamed cells or tissue. In other embodiments, the nanoparticles present on their surface, phosphatidyl serine incorporated into the nanoparticles in an effective amount to cause neutrophils to phagocytize the nanoparticles.

The targeting peptides can be associated with the polymer covalently, for example, via a linker cleaved at the site of delivery. In another embodiment, a diagnostic or imaging tag such as a fluorescent tag is chemically conjugated to a polymer to yield an imageable labeled polymer. Alternatively, or in addition, a therapeutic drug can be chemically conjugated to a polymer to yield a polymer-drug or polymer-imaging agent-drug conjugate. In certain embodiments, the drug can be covalently associated with polymer to yield a "polymer-drug conjugate". In certain embodiments, the hydrophilic portion of the polymer can be connected to the hydrophobic portion by a cleavable linker, the diagnostic, therapeutic or prophylactic agent can be connected to the amphiphilic polymer by a cleavable linker, and/or the targeting moiety can be connected to the amphiphilic polymer by a cleavable linker. The linker can be hydrolyzed by a chemical or enzymatic process. In certain embodiments, the linker is cleaved by hydrogen peroxide, which is produced at sites of inflammation or areas of high neutrophil concentration, thereby increasing the selectivity of the nanoparticles.

Also provided are methods of making the multimodal nanoparticles described herein. In one embodiment, the particles are formed by self-assembly of amphiphilic molecules having a hydrophobic portion and a hydrophilic portion, and the amphiphilic molecules having conjugated thereto a targeting moiety or a diagnostic agent or a therapeutic agent. In another embodiment, a polymer-peptide conjugate composed of end-to-end linkages between a polymer and a targeting peptide is prepared. The multimodal nanoparticles can be prepared using an emulsion solvent evaporation method. In another embodiment, multimodal nanoparticles are prepared using nanoprecipitation methods or microfluidic devices. In another embodiment, multimodal polymer/lipid hybrid nanoparticles are prepared by the self-assembly of polymers and macrophage-targeted lipid using emulsion solvent evaporation, a single-step nanoprecipitation method, or microfluidic devices. The lipid can be one or more of natural, synthetic and semi-synthetic phosphatidyl serine (PS) lipids, or combinations thereof. Lipids can be dissolved in one or more of the following: chloroform, dichloromethane, ethanol, methanol, isopropyl alcohol, acetonitrile and Dimethyl sulfoxide (DMSO). In some embodiments, the targeting lipids may not be covalently associated with the resulting particles. In other embodiments, the targeting lipids are covalently associated with the resulting particles by a linker. The lipids can also be associated with the surface of, encapsulated within, surrounded by, and/or distributed throughout the polymeric matrix of the particles.

The inflammation-targeted molecules, diagnostic or therapeutics can be associated with the surface of, encapsulated within, surrounded by, and/or distributed throughout the polymeric matrix.

The nanoparticles disclosed herein possess excellent stability, high loading efficiency, multiple agent encapsulation, targeting and imaging. They can be targeted to sites of, or associated with, inflammation caused by a disease, disorder; trauma, chemotherapy or radiation. In certain embodiments, the nanoparticles can bind to cells, collagen IV, or other components within atherosclerotic plaques to deliver therapeutics or imaging probes to atherosclerotic plaques. Accordingly, in some embodiments, the nanoparticles contain one or more therapeutic agents to alleviate one or more symptoms or causes of inflammation associated with or resulting from a disease, disorder; trauma, chemotherapy or radiation.

Also provided is method of treating excessive inflammation and failed resolution of the inflammatory response in conditions which include underlying components of numerous conditions such as autoimmune disorders like arthritis and systemic lupus erythematosis, cardiovascular disease, hepatitis, nephritis, asthma, obesity-related insulin resistance, neurodegenerative disease, and cancer. These nanoparticles can provide a selective means of treating inflammatory conditions, where the nanoparticles are targeted to the inflamed tissue to reduce inflammation and enhance resolution. The nanoparticles disclosed herein can also be used to deliver therapeutic agents to atherosclerotic plaques

BRIEF DESCRIPTION OF THE DRAWINGS

(FIG. 2B). PLGA-PEG-Mal (2) is then conjugated to the free thiol on the cysteine of the KLWVLPKGGGC (SEQ ID NO: 3) peptide sequence via thiol-maleimide chemistry, in DMF with triethylamine ($Et_3N$) and subsequently precipitated and washed with cold methanol to yield the PLGA-PEG-Col IV targeting polymer (3) (FIG. 2C). The diblock PLGA-Alexa 647 (FIG. 2D) is synthesized by conjugating Alexa 647 cadaverine to poly (DL-lactide-co-glycolide using similar conditions used to synthesize 1.

FIG. 3A shows dynamic light scattering measurements of empty, non-targeted (Ac2-26 NP), targeted (Ac2-26+Col IV NP), scrambled peptide (Scrm Ac2-26 NP), and targeted scrambled peptide (Scrm Ac2-26+Col IV NP) formulations (mean±SD, n=3). FIG. 3B is a measure of the zeta potential of the formulations in (A). FIG. 3C shows an in vitro cumulative release curve of Ac2-26 peptide from targeted and non-targeted NPs incubated at 37° C. (mean±SD, n=3). The released peptide at different time points was isolated by filtration, and the absorbance of these samples was measured at 220 nm.

FIG. 4A shows PMN infiltration in response to Ac2-26 NPs compared to controls, (n=3/treatment; mean±SEM). *p<0.05, **p<0.01 for zymosan vs. treatment; § p<0.05 for Ac2-26 NP vs. Ac2-26. FIG. 4B shows maximal PMN infiltration in response to Semi Ac2-26 NPs, (outermost line); vehicle (middle line); Ac2-26 NPs, (innermost line)) in mice. FIG. 4C shows resolution indices ($R_i$) for zymosan alone (top panel) and Ac2-26 NPs (bottom panel) (n=3/treatment mean±SEM). *p<0.05, **p<0.01 for zymosan vs. Ac2-26 NPs; § p<0.05 for Ac2-26 NP vs. Scrm Ac2-26.

(FIG. 6A) The size distribution (nm) of $TNP_{LyP-1}$ determined by dynamic light scattering (DLS) are shown in FIG. 6B.

DETAILED DESCRIPTION OF THE INVENTION

Figure 1A:
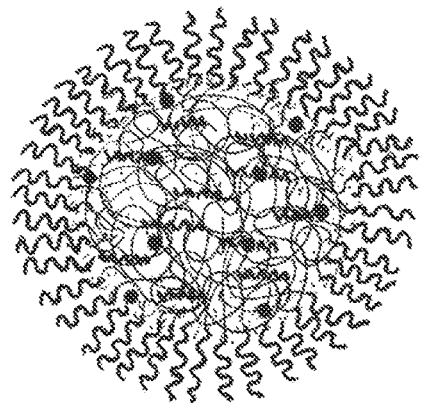
FIGS. 1A-1D show nanoparticle design and formulation. Targeted (FIGS. 1B, 1D) and non-targeted (FIGS. 1A, 1C) nanoparticles (NPs) encapsulating the Ac2-26 peptide (FIGS. 1A, 1B) or scrambled Ac2-26 peptide (FIGS. 1C, 1D) formulated using di and triblock biodegradable polymers via a single step nanoprecipitation are shown. (Scrm=scrambled).

Nanoparticle (NP) mediated delivery of therapeutics (nanomedicine) is a rapidly expanding field, and numerous bioactive molecules and imaging agents have been successfully delivered to sites of disease (Farokhzad, et al. *Cancer Res* 64(21):7668-7672 (in eng) (2004)). Farokhzad, et al. *Prot Natl Acad Sci USA* 103(16):6315-6320 (2006)). Hrkach, et al. *Sci Transl Med* 4(128):128ra139 (2012)). SPMs incorporated into NPs derived from human PMNs were shown to limit acute inflammation, enhance resolution and reduce joint damage. (Norling, et al., *J Immunol.*, 186(10):5543-5547 (2011)).

Challenges associated with current nanocarriers include low encapsulation efficiency of the payload, lack of sustained release of carried drugs, poor blood circulation half-life, and lack of selectivity to biomarkers of interest on cells, tissues, or organs of the body. These issues can impede extensive applications of these nanoparticles. A micro/nanoparticle platform technology has been developed in response to these needs.

The Examples demonstrate the pro-resolving activity of nanoparticles (NPs) containing the anti-inflammatory peptide Ac2-26, an annexin A1/lipocortin 1-mimetic peptide. These NPs were formulated using biodegradable diblock poly(lactic-co-glycolic acid-b-polyethyleneglycol) PLGA-PEG and triblock PLGA-PEG-collagen IV (Col IV) targeted polymers. A self-limited zymosan-induced peritonitis model was used to show that the Ac2-26 NPs were smore potent than Ac2-26 native peptide at limiting recruitment of polymononuclear neutrophils (PMN) and decreasing the resolution interval. Moreover, in hind-limb ischemia-reperfusion injury, systemic administration of A2-26-CoIV NPs blocked tissue damage. Together, these findings demonstrate that Ac2-26 NPs are anti-inflammatory and pro-resolving in vivo.

I. Definitions

"Binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions.

"Binding partner" as used herein refers to a molecule that can undergo binding with a particular molecule.

"Biological binding" defines a type of interaction that occurs between pairs of molecules including proteins, peptides, nucleic acids, glycoproteins, carbohydrates, or endogenous small molecules.

A "biocompatible polymer" is used here to refer to a polymer that does not typically induce an adverse response when inserted or injected into a living subject, for example, without significant inflammation and/or acute rejection of the polymer by the immune system, for instance, via a T-cell response.

A "copolymer" herein refers to more than one type of repeat unit present within the polymer defined below.

"Encapsulation efficiency" (EE) as used herein is the fraction of initial drug that is encapsulated by the nanoparticles (NPs).

"Peptide loading" as used herein refers to the mass fraction of peptide in the NPs.

A "polymer," as used herein, is given its ordinary meaning as used in the art, i.e., a molecular structure including one or more repeat units (monomers), connected by covalent bonds.

A "polymeric conjugate" as used herein refers to two or more polymers (such as those described herein) that have been associated with each other, usually by covalent bonding of the two or more polymers together.

"Specific binding" as used herein refers to molecules, such as polynucleotides, that are able to bind to or recognize a binding partner (or a limited number of binding partners) to a substantially higher degree than to other, similar biological entities.

II. Compositions

The multimodal nanoparticles described herein have four main components: 1) a targeting element (peptides, lipids, antibodies, small molecules, etc.) that can bind to a unique molecular signature on cells, tissues, or organs of the body; 2) a fluorophore or NMR contrast agent that allows visualization of nanoparticles within plaques and/or therapeutic or prophylactic agents; 3) an outside stealth layer that can allow the particles to evade recognition by immune system components and increase particle circulation half-life; 4) a biodegradable polymeric material, forming an inner core which can carry therapeutics and release the payloads at a sustained rate after systemic, intraperitoneal, oral or pulmonary administration The polymeric inner core efficiently encapsulates therapeutic molecules or imaging agents including genes, proteins, peptides, small molecules and NMR contrast agents. The functional groups on the polymers enable covalent conjugation of therapeutic molecules or imaging agents, further enhancing the encapsulation yield and slow drug release. An outer sheath layer covers the polymeric core. By covering the nanoparticle with a stealth layer, the nanoparticles remain in the bloodstream long enough to reach or recognize their therapeutic site of action.

There are at least two methods to incorporate targeting moieties into the nanoparticles: i) conjugation of targeting ligands to the hydrophilic or "stealth" region (e.g. PEG) of polymers prior to nanoparticle preparation; and ii) incorporation of targeting molecules into nanoparticles while the stealth layer on the nanoparticle surface can be cleaved in the presence of a chemical or enzyme at tissues of interest to expose the targeting molecules.

The polymeric NP design incorporates biocompatible, biodegradable, and bioeliminable materials and can make use of a self-assembly approach. Conventional methods of formulating targeted NPs involve a series of synthetic coupling steps involving the bioconjugation of targeting ligands to the surface of preformed NP cores (Kamaly, et al., *Chem Soc Rev* 41(7):2971-3010 (2012)). This post-coupling of targeting ligands requires excessive amounts of reagents in order to achieve high coupling efficiencies and requires further NP purification techniques to remove unbound ligands. As such, heterogeneity may arise in the reproducibility of NP surface properties and ligand densities, resulting in batch-to-batch variability, which may hinder successful clinical translation and subsequent commercialization The design of pre-functionalized triblock copolymers allows for the reproducible creation of optimal targeted NPs, whereby controlling the self-assembly and ratio of each constituent can lead to targeted polymeric NPs with precisely tuned biophysicochemical properties (Gu, et al., *Proc Natl Acad Sci USA*, 105(7):2586-2591 (2008)). The use of diblock or triblock hydrophobic-PEGylated polymers in nanoprecipitation leads to NPs that consist of a hydrophobic core, with entrapped therapeutics surrounded by a hydrophilic PEG shell for steric stabilization and prolonged systemic circulation (Mora-Huertas et al. *Int J Pharm* 385(1-2):113-142). In nanoprecipitation, the instantaneous formation of particles is governed by the principles of the Marangoni effect and has been attributed to interfacial interactions between liquid phases (Quintanar-Guerrero, et al. *Drug Dev Ind Pharm* 24(12):1113-1128 (1998)). Nanoprecipitation is a simple method, amenable to scale-up at an industrial scale and requires only mild mixing under minimal sheer stress. In general, smaller NPs are obtained through this method when compared with other methods under equivalent conditions.

The particles described herein can be used to selectively deliver therapeutic compounds or imaging agents into atherosclerotic plaques, providing great benefits in the treatment and imaging of atherosclerosis and cardiovascular diseases, as well as the treatment of other diseases such as cancer.

NPs self-assembled from biodegradable poly(lactide-co-glycolide)-b-poly(ethylene glycol) (PLGA-b-PEG) block copolymers represent a promising class of potential delivery vehicles due to several unique properties: PLGA-b-PEG copolymers i) are biocompatible and biodegradable and used in many FDA approved products, ii) are capable of encapsulating small- and macro-molecular payloads with a wide range of physiochemical properties, and iii) can be designed for controlled release through a combination of polymer degradation and drug diffusion (Farokhzad, *Expert Opin Drug Deliv* 5(9):927-929 (2008)). The homing to the disease site is driven by the particles' nano-dimensions and PEGylated surface through the enhanced permeability and retention (EPR) effect (Peer, et al. *Nat Nanotechnol.,* 2(12):751-760 (2007)).

A. Polymers

Polymers are versatile building blocks for NP synthesis as they can be custom synthesized with unique biocompatibility and degradation properties (Kamaly, et al., *Chem Soc Rev* 41(7):2971-3010 (2012)). Their physicochemical properties can be easily manipulated, allowing for the formulation of self-assembled and customizable therapeutic controlled release NPs (Makadia, et al., *Polymers (Basel)* 3(3):1377-1397 (2011); Chan et al *Methods Mol Biol* 624:163-175; Farokhzad, et al. *Proc Natl Acad Sci USA* 103(16):6315-6320 (2006); Gu, et al., *Proc Natl Acad Sci USA* 105(7): 2586-2591 (2008)).

Polymers that can be used to make the NPs disclosed herein can have repeating units may all be identical, or in some cases, there may be more than one type of repeat unit present within the polymer. In some cases, the polymer is biologically derived, i.e., a biopolymer. Non-limiting examples include peptides or proteins (i.e., polymers of various amino acids), or nucleic acids such as DNA or RNA, as discussed below. In some cases, additional moieties may also be present in the polymer, for example biological moieties such as those described below.

The polymer being employed may be a copolymer in some cases. The repeat units forming the copolymer may be arranged in any fashion. For example, the repeat units may be arranged in a random order, in an alternating order, or as a "block" copolymer, i.e., including one or more regions each including a first repeat unit (e.g., a first block), and one or more regions each including a second repeat unit (e.g., a second block), etc. Block copolymers may have two (a diblock copolymer), three (a triblock copolymer), or more numbers of distinct blocks.

Polymers and copolymers that can be used to make the nanoparticles disclosed herein include but are not limited to homopolymers including glycolic acid units, referred to herein as "PGA", and lactic acid units, such as poly-L-Iactic acid, poly-D-Iactic acid, poly-D,L-Iactic acid, poly-L-Iactide, poly-D-Iactide, and poly-D,L-Iactide, collectively referred to herein as "PLA", and caprolactone units, such as poly(8-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers".

In some embodiments the NPs can employ polymeric conjugate. A polymeric conjugate may include a first polymer and a second polymer, which have been conjugated together to form a block copolymer where the first polymer is a first block of the block copolymer and the second polymer is a second block of the block copolymer. Those of ordinary skill in the art will understand that a block copolymer may contain multiple blocks of polymer, and that a "block copolymer," is not limited to only block copolymers having only a single first block and a single second block. A block copolymer may include a first block including a first polymer, a second block including a second polymer, and a third block including a third polymer or the first polymer, etc. In some cases, block copolymers can contain any number of first blocks of a first polymer and second blocks of a second polymer (and in certain cases, third blocks, fourth blocks, etc.). Block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or other moieties (e.g., to non-polymeric moieties).

The polymeric conjugate is amphiphilic, i.e., having a hydrophilic portion and a hydrophobic portion, or a relatively hydrophilic portion and a relatively hydrophobic portion. A hydrophilic polymer is one generally that attracts water and a hydrophobic polymer is one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about 60°). In some cases, the hydrophilicity of two or more polymers may be measured relative to each other, i.e., a first polymer may be more hydrophilic than a second polymer. For instance, the first polymer may have a smaller contact angle than the second polymer.

The polymer is preferably a biocompatible polymer. One simple test to determine biocompatibility is to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers include polydioxanone (PDO), polyhydroxyalkanoate, polyhydroxybutyrate, poly(glycerol sebacate), polyglycolide, polylactide, polycaprolactone, or copolymers or derivatives including these and/or other polymers.

The biocompatible polymer is preferably biodegradable, i.e., the polymer is able to degrade, chemically and/or biologically, within a physiological environment, such as within the body. Examples of biodegradable polymers include, but are not limited to, poly(lactide) (or poly(lactic acid)), poly(glycolide) (or poly(glycolic acid)), poly(orthoesters), poly(caprolactones), polylysine, poly(ethylene imine), poly(acrylic acid), poly(urethanes), poly(anhydrides), poly(esters), poly(trimethylene carbonate), poly(ethyleneimine), poly(acrylic acid), poly(urethane), and poly(beta amino esters), and copolymers or derivatives of these and/or other polymers, for example, poly(lactide-co-glycolide) (PLGA).

In other embodiments, a polymeric conjugate includes a polymer able to control immunogenicity, for example, a poly(alkylene glycol) (also known as poly(alkylene oxide)), such as poly(propylene glycol), or poly(ethylene oxide), also known as poly(ethylene glycol) ("PEG"), having the formula $-(CH_2-CH_2-O)_n-$, where n is any positive integer. The poly(ethylene glycol) units may be present within the polymeric conjugate in any suitable form. PLURONIC®s, block copolymers of polyalkylene oxide-polypropylene oxid can also be used. For instance, the polymeric conjugate may be a block copolymer where one of the blocks is poly(ethylene glycol). A polymeric conjugate containing poly(ethylene glycol) repeat units is also referred to as a "PEGylated" polymer. Such polymers can control inflammation and/or immunogenicity (i.e., the ability to provoke an immune response), due to the presence of the poly(ethylene glycol) groups.

PEGylation may also be used, in some cases, to decrease charge interaction between a polymer and a biological moiety, e.g., by creating a hydrophilic layer on the surface of the polymer, which may shield the polymer from interacting with the biological moiety. In some cases, the addition of poly(ethylene glycol) repeat units may increase plasma half-life of the polymeric conjugate, for instance, by decreasing the uptake of the polymeric conjugate by the phagocytic system while decreasing transfection/uptake efficiency by cells. Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, as discussed in the examples below, by ring opening polymerization techniques (ROMP).

B. Lipids

The nanoparticles described herein may also contain a lipid moiety. As described by Zwaal, et al. *CMLS, Cell. Mol. Life Sci.*, 62:971-988 (2005), phosphatidylserine (PS) is one of the four major phospholipids that predominates in the plasma membranes of mammalian cells, typically comprising 8-15 mole % of the total phospholipid content. In quiescent cells, it is exclusively located at the cytoplasmic side of the membrane bilayer together with most of the phosphatidylethanolamine (PE), whereas the outer monolayer is mainly composed of phosphatidylcholine (PC) and sphingomyelin (Sph). When cells are activated, or enter apoptosis, lipid asymmetry can be perturbed by other lipid transporters (scramblases) that shuttle phospholipids non-specifically between the two monolayers. This exposes phosphatidylserine (PS) at the cells' outer surface. Since PS promotes blood coagulation, defective scramblase activity upon platelet stimulation causes a bleeding disorder (Scott syndrome). PS exposure also plays a pivotal role in the recognition and removal of apoptotic cells via a PS-recognizing receptor on phagocytic cells.

Expression of PS at the cell surface can occur in a wide variety of disorders. As demonstrated by the examples, it is possible to target phosphatidyl serine ("PS"), which is exposed on the surface of cells during inflammation. Apoptotic cells are quickly recognized and engulfed by phagocytes to prevent the release of noxious materials from dying cells. PS exposed on the surface of apoptotic cells is an "eat-me" signal for the phagocytes.

Accordingly, one or more of natural, synthetic and semi-synthetic phosphatidylserine (PS) lipids, or combinations thereof, can be bound onto the surface, conjugated to the polymers forming the nanoparticles or inserted into the particles during self-assembly, so that the nanoparticles will be preferentially phagocytosed by neutrophils.

C. Targeting Agents

The NPs may include a targeting moiety, i.e., a moiety able to bind to or otherwise associate with a biological entity, for example, a membrane component, a cell surface receptor, or a molecule associated with the inflamed tissue or site of inflammation.

In one embodiment, the targeting moiety has a specificity (as measured via a disassociation constant) of less than about 1 micromolar, at least about 10 micromolar, or at least about 100 micromolar. The NPs may be targeted to a site of, or tissue associated with, inflammation. In some embodiments, the target site is neutrophils, which may phagocytize the NPs to release a therapeutic and/or diagnostic agent at the site of inflammation.

Numerous examples of targeting moieties are known, some of which are more selective than others. Proteins constitutively expressed on the surface of neutrophils that are important for recognition of the endothelial inflammatory signals include the glycoprotein P-selectin glycoprotein ligand-1 (PSGL-1) and L-selectin.

Other agents to be targeted include those associated with the disease. For example, a plaque targeted peptide can be one or more of the following: Collagen IV, CREKA (SEQ ID NO: 1), LyP-I, CRKRLDRNC (SEQ ID NO: 2), or their combinations at various molar ratios. The targeting peptides are covalently associated with the polymer, for example, via a linker cleaved at the site of delivery.

D. Therapeutic, Diagnostic, and Prophylactic Agents

Therapeutic agents that may be delivered using the nanoparticles described herein can be proteins, peptides, carbohydrates, nucleic acid molecules or combinations thereof, or low molecular weight compounds. Therapeutic agents can include anti-inflammatories, immunosuppressants, or more specific drugs for inhibition of the disease or disorder to be treated. These may be administered in combination, for example, a general anti-inflammatory with a specific biological targeted to a particular receptor. One may administer an agent in treatment for ischemia that restores blood flow, such as an anticoagulant, anti-thrombotic or clot dissolving agent such as tissue plasminogen activator, as well as an anti-inflammatory. A chemotherapeutic which selectively kills cancer cells may be administered in combination with an anti-inflammatory that reduces swelling and pain or clotting at the site of the dead and dying tumor cells.

In some embodiments the nanoparticles can include SPMs such as lipoxins, resolvins, protectins, maresins, and specific protein mediators such as annexin A1 and the active peptide derivatives of these proteins.

Examples of useful biological anti-inflammatories include, but are not limited to, adalimumab (HUMIRA®), etanercept (ENBREL®), and infliximab (REMICADE®). Anti-inflammatory peptides include, but are not limited to, those described in U.S. Pat. Nos. 7,153,835; 7,094,760; 6,586,403; 6,852,697; WO03066670; and WO9806742. These include sub-mandibular gland peptide (T(SGP-T) which regulates immune responses on exposure to an endotoxin, phenylalanine-glutamine-glycine peptide (FEG) which inhibits cell receptors and regulates the leukocytes and prevents tissue infiltration, as well as decreases neutrophils and eosinophils in an immune response.

Small molecule non-steroidal anti-inflammatory drugs (NSAIDs) include, but are not limited to, ibuprofen, naproxen, aspirin, ketoprofen, diclofenac, indomethacin, piroxicam, meloxicam, sulindac, methotrexate, leflunomide, hydroxychloroquine, and sulfasalazine. Small molecule steroidal anti-inflammatories include, but are not limited to, prednisone, dexamethasone, cortisone, and fluticasone. Others are known to those skilled in the art, for example, as described in Goodman and Gilmans.

Examples for treatment of atherosclerotic plaques include, but are not limited to, antiinflammatory agents/cytokines (e.g. AZ876, 3-(3-(2-chloro-3-trifluoromethyl-benzyl-2,2diphenylethylamino)proproxy), phenylacetic acid (GW3965), 25-Hydroxycholesterol (HI 015), 22(R)-hydroxycholesterol (H9384), 22(S)-hydroxycholesterol (H5884), N,N-dimethyl-3-hydroxycholenamide (DMHCA), T0901317 [N-(2,2,2,-trifluoro-ethyl)-N-[4-(2,2,2,-trifluoro-1hydroxy-1-trifluoromethyl-ethyl)-phenyl]benzenesulfonamide], hypocholamide, etc.), HMGCoA reductase inhibitors (atorvastatin, Atorvastatin, Amlodipine Besylate, Cerivastatin, Fluvastatin, Lovastatin, Mevastatin, Pitavastatin, Pravastatin, Rosuvastatin, Simvastatin, etc.), RNA, DNA, chemotherapeutic compounds, chemical or biologic inhibitors of inflammatory cytokines, their receptors, or their signaling intermediates, or combinations thereof.

The examples demonstrate the delivery and bioactions of polymeric NPs encapsulating Act-26, an annexin A1 N-terminal mimetic peptide that acts on the G-protein coupled formyl peptide receptor, ALX/FPR2 (Perrettiet, et al. *Nat Rev Immunol* 9(1):62-70 (2009); Dufton, et al. *J Immunol* 184(5):2611-2619 (2010)), which is also the receptor for lipoxin A4 (Perretti, et al., *Nat Med* 8(11):1296-1302 (2002)). Act-26 exerts anti-inflammatory (Perretti, et al., *Am J Pathol* 158(6):1969-1973 (2001)) and pro-resolving actions in vivo and was shown to be protective in several disease models, including myocardial ischemia-reperfusion injury (La, et al. *FASEB J,* 15(12):2247-2256 (2001)), allergic inflammation (Bandeira-Melo, et al. *J Pharmacol Exp Ther* 313(3):1416-1422 (2005)), and endotoxin-induced cerebral inflammation (Gavins, et al., *FASEB J* (2012)).

Ac2-26 and Resolvin D1 (RvD1), an anti-inflammatory and proresolving molecule (Rius et al., *FASEB J.* 2014 February; 28(2):836-48. Epub 2013 Nov. 18), may be useful to promote the resolution initiated by calorie restriction in obesity-induced steatohepatitis by reducing the inflammatory component of obesity-induced NASH.

E. Imaging Agents

An imaging, detectable or sensing moiety, i.e., a moiety that can be determined in some fashion, either directly or indirectly, may be bound to the NPs or to the polymers Ruining the NPs. Representative imaging entities include, but are not limited to, fluorescent, radioactive, electron-dense, magnetic, or labeled members of a binding pair or a substrate for an enzymatic reaction, which can be detected. In some cases, the imaging entity itself is not directly determined, but instead interacts with a second entity in order to effect determination; for example, coupling of the second entity to the imaging entity may result in a determinable signal. Non-limiting examples of imaging moieties include, but are not limited to, fluorescent compounds such as FITC or a FITC derivative, fluorescein, green fluorescent protein ("GFP"), radioactive atoms such as $^3$H, $^{14}$C, $^{33}$P, $^{32}$P, $^{125}$I, $^{131}$I, $^{35}$S, or a heavy metal species, for example, gold or osmium. As a specific example, an imaging moiety may be a gold nanoparticle. A diagnostic or imaging tag such as a fluorescent tag is chemically conjugated to a polymer to yield a fluorescently labeled polymer.

F. Linkers

In different embodiments, the hydrophilic portion of the polymer can be connected to the hydrophobic portion by a cleavable linker, the diagnostic, therapeutic or prophylactic agent may be connected to the amphiphilic polymer by a cleavable linker, and/or the targeting moiety may be connected to the amphiphilic polymer by a cleavable linker. The linker may be hydrolyzed by a chemical or enzymatic process. Preferably, the linker is cleaved by hydrogen peroxide, which is produced at sites of inflammation or areas of high neutrophil concentration, thereby increasing the selectivity of the nanoparticles. For example, the linker may be hydrolyzed by a chemical or enzymatic process.

Since the nanoparticles are targeted to sites or tissues involved in an inflammatory process, the linker is preferably can be cleaved by enzymes present in, or released by, neutrophils at the site of inflammation. There are three fundamental types of granules in neutrophils. Azurophilic granules (also known as peroxidase-positive or primary granules) are the largest, measuring approximately 0.3 µM in diameter, and are the first formed during neutrophil maturation. They are named for their ability to take up the basic dye azure A and contain myeloperoxidase (MPO), an enzyme critical in the oxidative burst. Other cargo of this granule class include the defensins, lysozyme, bactericidal/permeability-increasing protein (BPI), and a number of serine proteases: neutrophil elastase (NE), proteinase 3 (PR3), and cathepsin G (CG). Upon activation, neutrophils produce ROS in a process called the respiratory burst. It is misleading to think of ROS as a single entity because they differ in their stability, reactivity, and permeability to membranes. However, all ROS can modify and damage other molecules, properties exploited by the host cell for signaling and antimicrobial action. The NADPH oxidase complex assembles on the phagosomal and plasma membranes and begins the reactive oxygen cascade by reducing molecular oxygen to superoxide. Downstream of superoxide, many potential reactions can occur. Superoxide, though not a strong oxidant, rapidly dismutates, forming hydrogen peroxide. Superoxide can also react with nitric oxide, which is produced at high levels at inflammatory sites, to form peroxynitrite, a strong oxidant. Upon degranulation into the phagosome, MPO can react with hydrogen peroxide to produce various reactive species, including hypohalous acids. See, for example, Amulic, et al. Annu. Rev. Immunol 2012. 30:459-89.

III. Methods of Making Nanoparticles

Methods of preparing these nanoparticles are described. In one embodiment, multimodal nanoparticles are prepared using emulsion solvent evaporation method. A polymeric material is dissolved in a water immiscible organic solvent and mixed with a drug solution or a combination of drug solutions. The water immiscible organic solvent can be one or more of the following: chloroform, dichloromethane, and acyl acetate. The drug can be dissolved in, but is not limited to, one or a plurality of the following: acetone, ethanol, methanol, isopropyl alcohol, acetonitrile and Dimethyl sulfoxide (DMSO). An aqueous solution is then added into the resulting mixture solution to yield emulsion solution by emulsification. The emulsification technique can be, but not limited to, probe sonication or homogenization through a homogenizer. The plaque-targeted molecules or fluorophores or drugs may be associated with the surface of, encapsulated within, surrounded by, and/or distributed throughout the polymeric matrix of this inventive particle.

In another embodiment, multimodal nanoparticles are prepared using nanoprecipitation methods or microfluidic devices. A polymeric material is mixed with a drug or drug combinations in a water miscible organic solvent. The water miscible organic solvent can be one or more of the following: acetone, ethanol, methanol, isopropyl alcohol, acetonitrile and Dimethyl sulfoxide (DMSO). The resulting mixture solution is then added to an aqueous solution to yield nanoparticle solution. The plaque-targeted peptides or fluorophores or drugs may be associated with the surface of, encapsulated within, surrounded by, and/or distributed throughout the polymeric matrix of the particles.

In another embodiment, multimodal polymer/lipid hybrid nanoparticles are prepared by the self-assembly of polymers and macrophage-targeted lipid using emulsion solvent evaporation, a single-step nanoprecipitation method, or microfluidic devices. The lipid is one or more of natural, synthetic and semi-synthetic phosphatidylserine (PS) lipids, or combinations thereof. Lipids can be dissolved in one or more of the following: chloroform, dichloromethane, ethanol, isopropyl alcohol, acetonitrile and Dimethyl sulfoxide (DMSO). In some embodiments, the targeting lipids may not be covalently associated with the resulting particles. In certain embodiments, the targeting lipids are covalently associated with the resulting particles by a linker. In certain embodiments, lipids may be associated with the surface of, encapsulated within, surrounded by, and/or distributed throughout the polymeric matrix of the particles.

Two methods to incorporate targeting moieties into the nanoparticles include: i) conjugation of targeting ligands to the hydrophilic region (e.g. PEG) of polymers prior to nanoparticle preparation; and ii) incorporation of targeting molecules into nanoparticles while the stealth layer on the nanoparticle surface can be cleaved in the presence of a chemical or enzyme at tissues of interest to expose the targeting molecules.

The targeting efficacy of NPs varies with the weight ratio of non-functionalized and ligand-modified polymers. NPs with a fixed polymer/polymer-peptide weight ratio of up to 39 were used to achieve optimal targeting capabilities and physiochemical properties.

EXAMPLES

1) Synthesis of Polymer-Peptide Conjugates

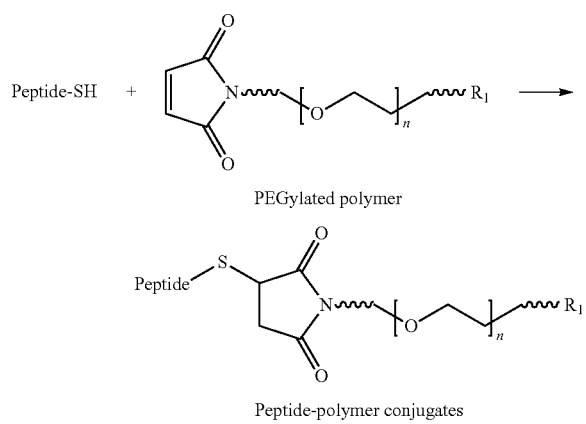

Synthesis of polymer-peptide conjugates

PEGylated polymer

Peptide-polymer conjugates

R1 = PGA, PLA, PCL, or their copolymers such as PLGA, or other polyesters
Peptide = CREKA, LyP-1, CRKRLDRNC, or their combinations at various molar ratios

2) Synthesis of Fluorescently Labeled Polymer

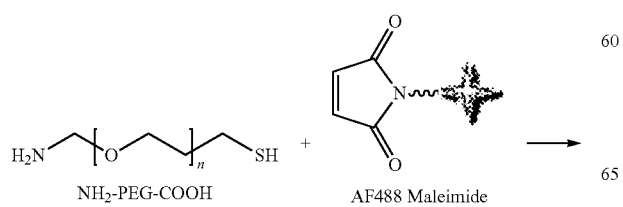

Synthesis of PLGA-PEG-AF488

NH2-PEG-COOH   AF488 Maleimide

NH2-PEG-AF 488 Conjugates

PLGA

PLGA-PEG-AF 488

3) Synthesis of Polymer-Drug Conjugates

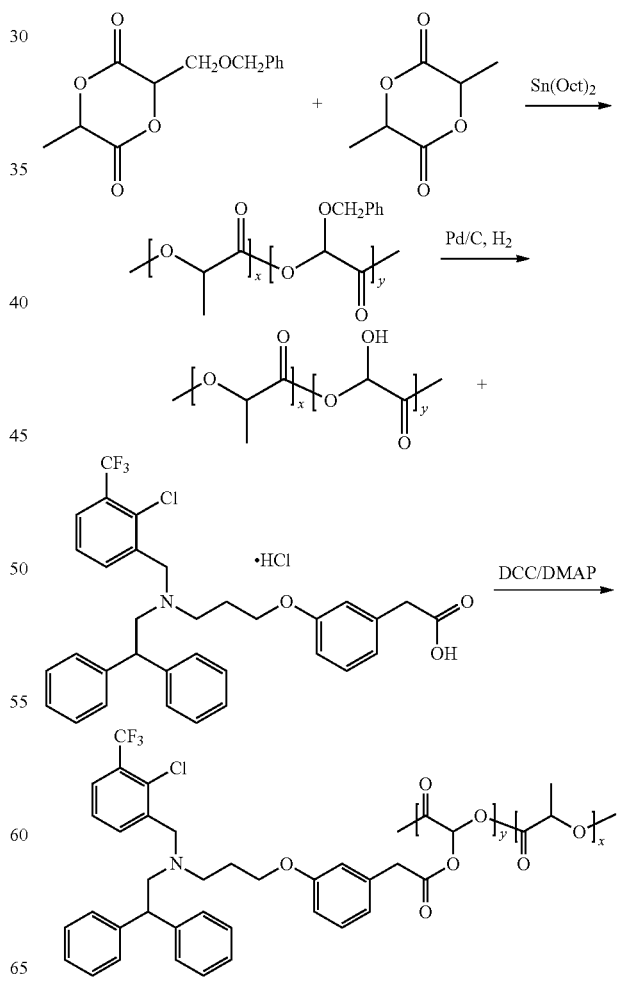

Synthesis route 1

Synthesis Route 2.
GW3965 is covalently associated with PLGA-PEG copolymer by a linker which can be cleaved in the presence of hydrogen peroxide.
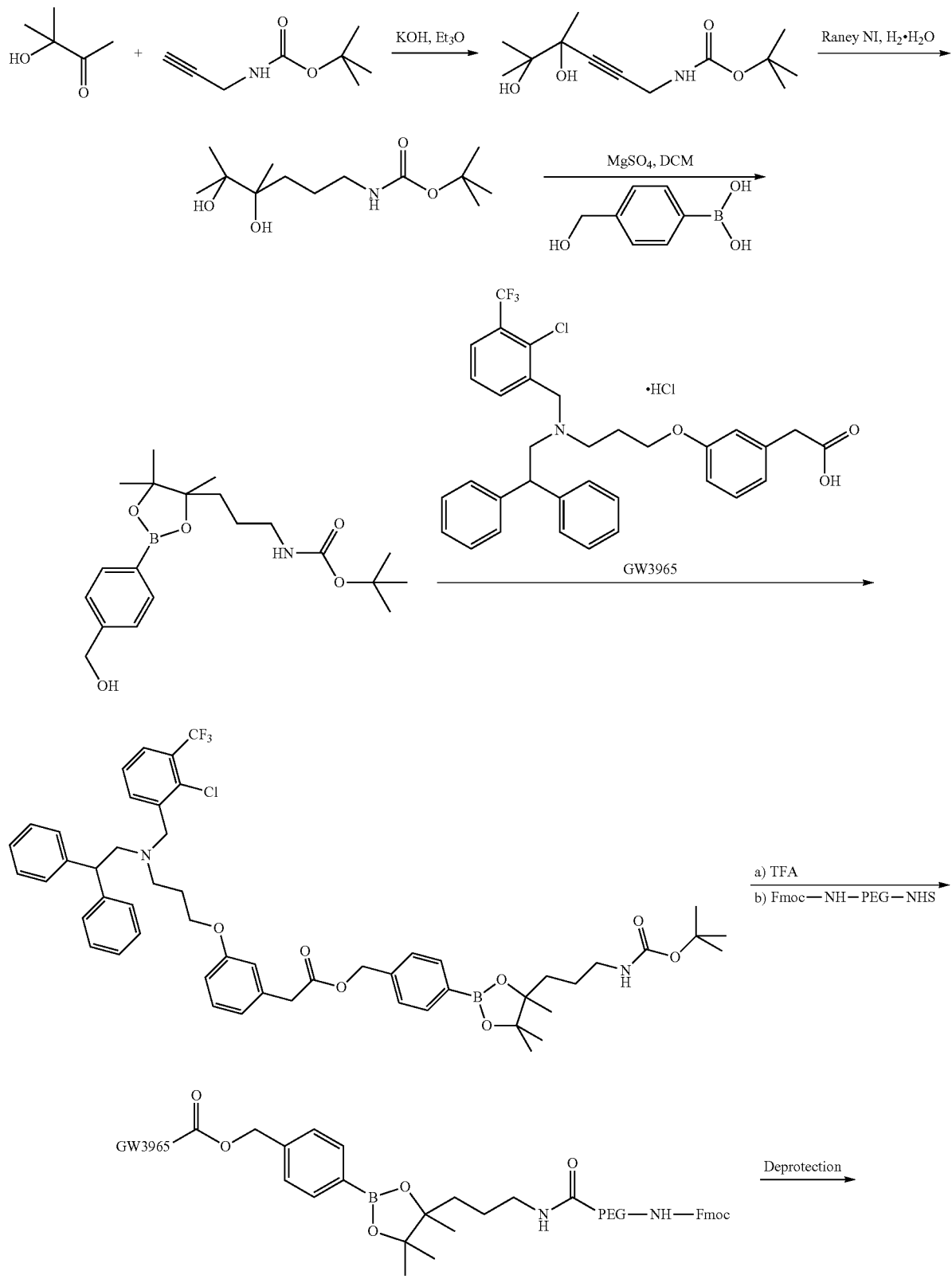

-continued
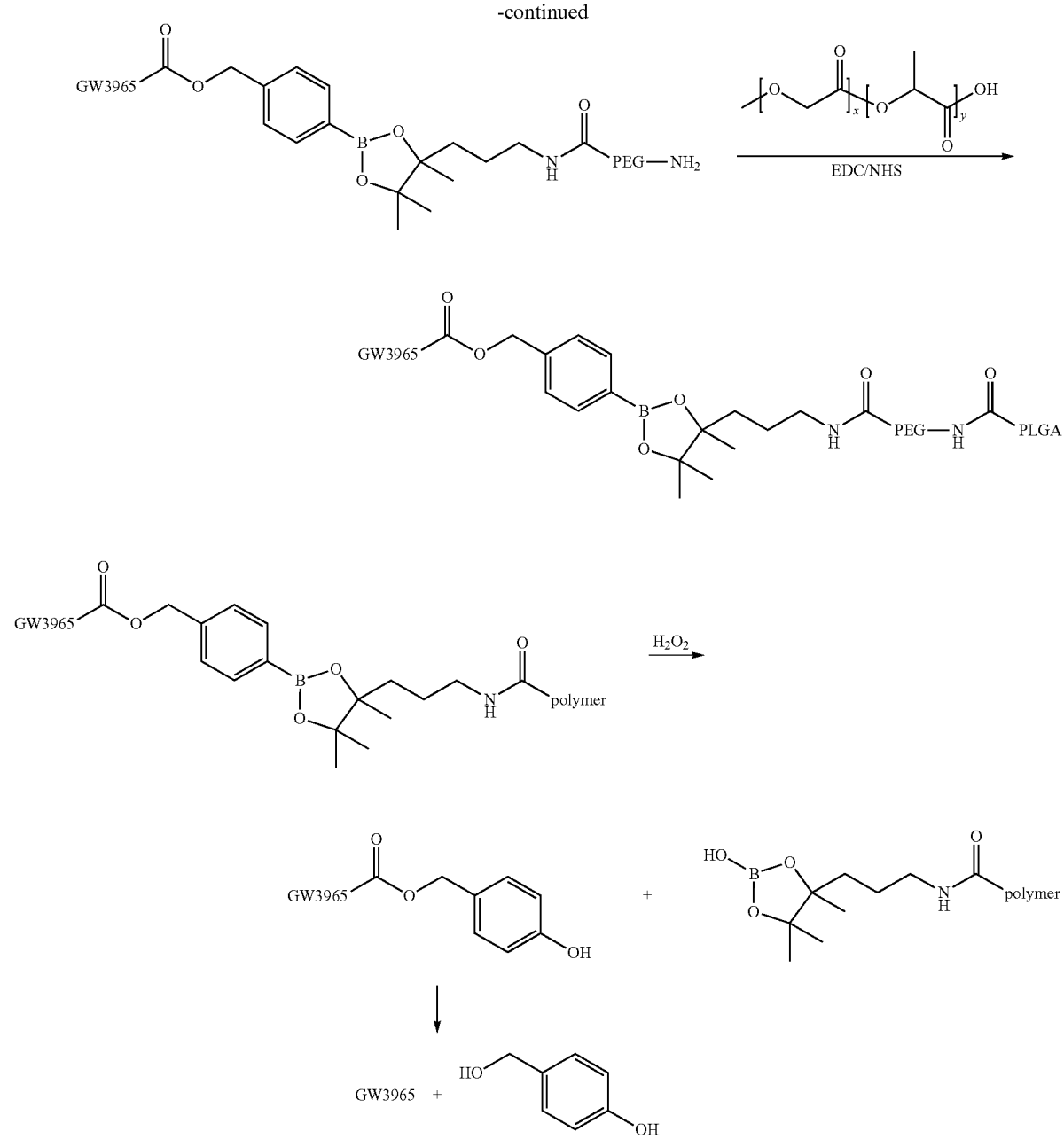
4) Synthesis of polymer-PEG conjugate. PEG is covalently associated with PLGA polymer by a linker which can be cleaved in the presence of hydrogen peroxide.
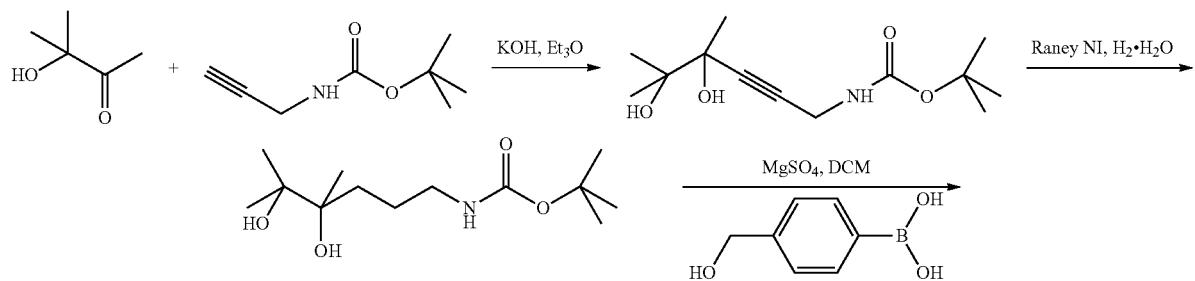

21 22
-continued
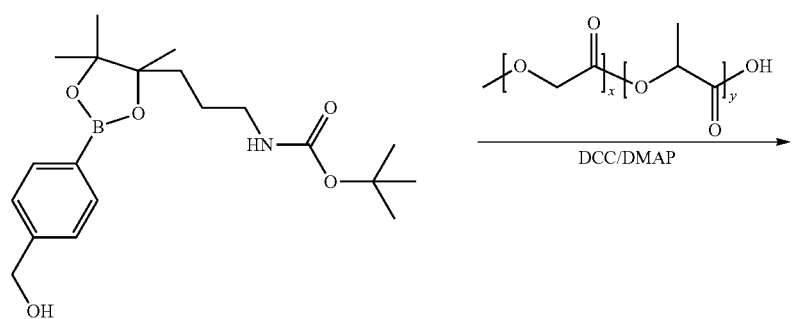
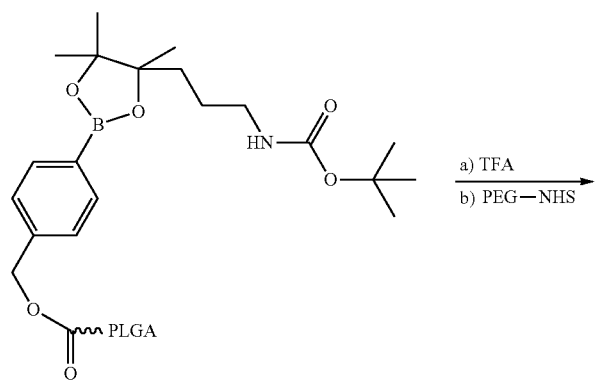
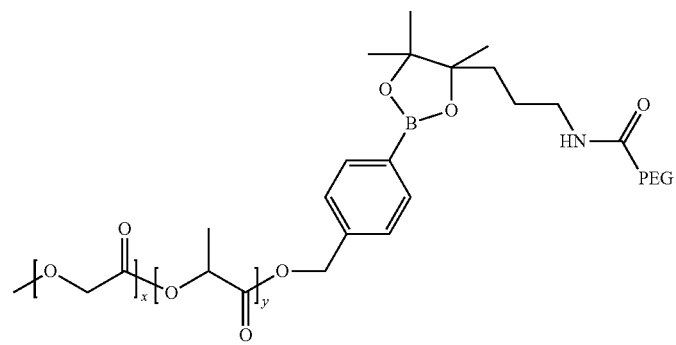
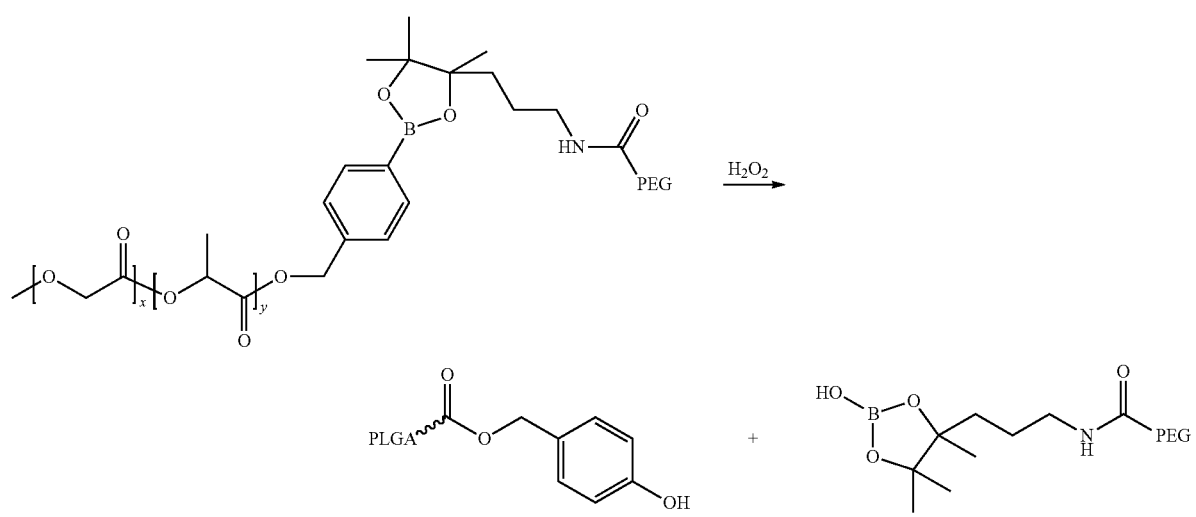

5) Synthesis of polymer-lipid conjugate. PS lipid is covalently associated with PLGA-PEG copolymer by a linker which can be cleaved in the presence Pf hydrogen peroxide.
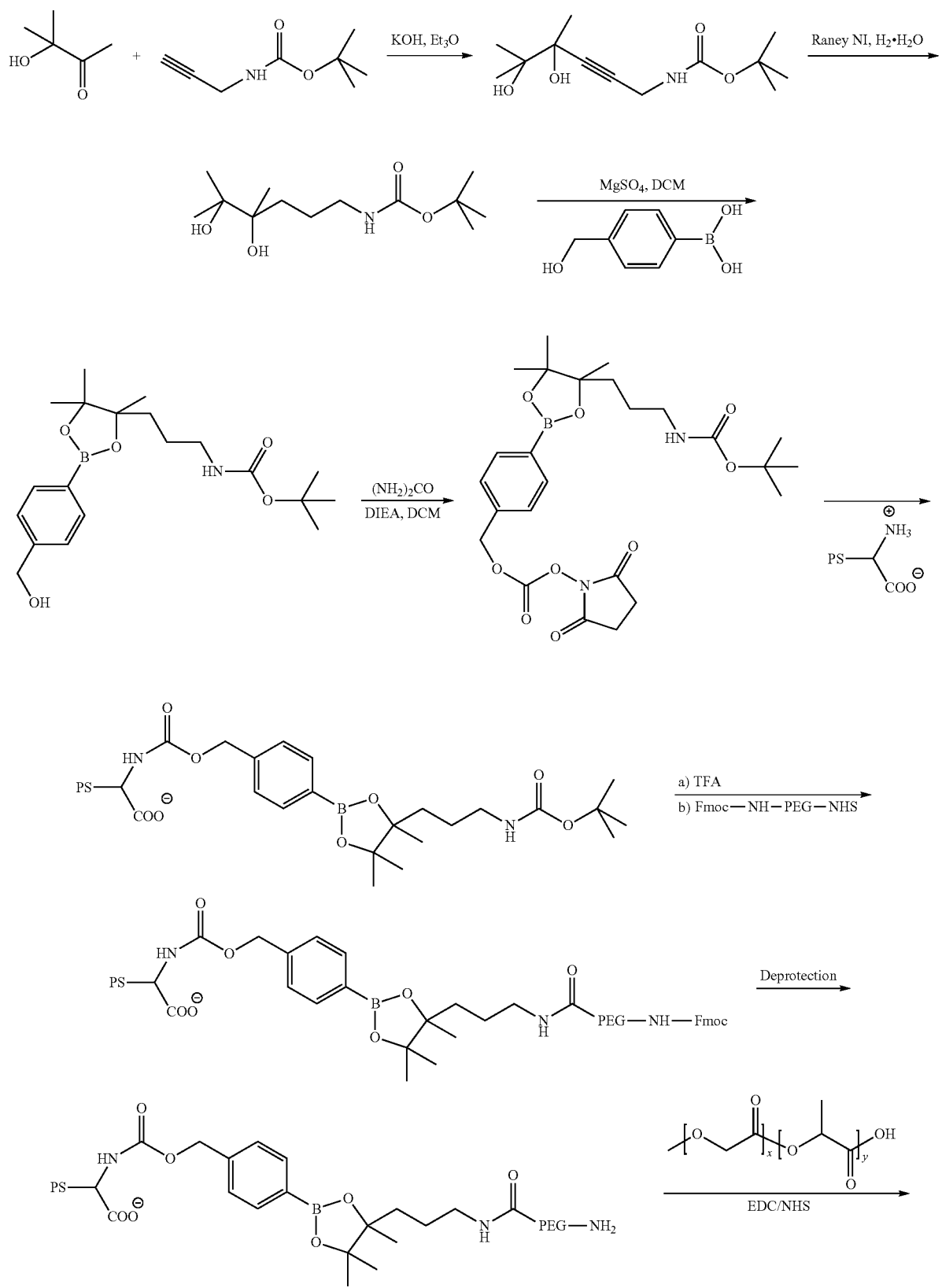

-continued

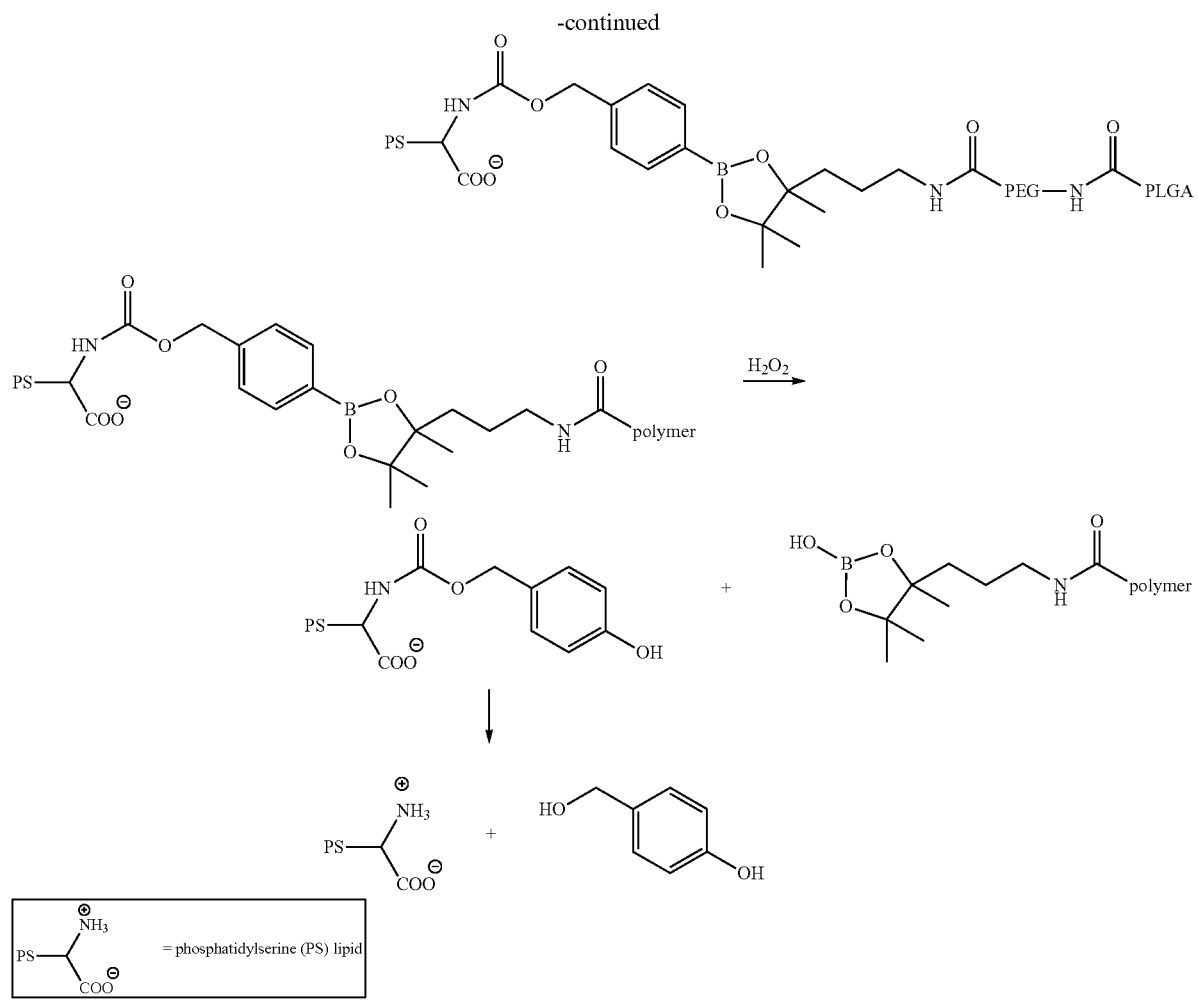

6) Schematic diagram of peptide-functionalized nanoparticles. The particle is composed of an inner core formed by biodegradable polymer which can encapsulate drugs and imaging probes and release drugs at a sustained rate. The outer PEG-peptide or PEG-fluorophore layer facilitates immune evasion and allows targeting and visualization of nanoparticles within plaques.

The targeting efficacy of NPs varies with the weight ratio of non-functionalized and ligand-modified polymers. NPs with a fixed polymer/polymer-peptide weight ratio up to 39 were used to achieve optimal targeting capabilities and physiochemical properties.

NPs self-assembled from biodegradable poly(lactide-co-glycolide)-b-poly(ethylene glycol) (PLGA-b-PEG) block copolymers represent a promising class of potential delivery vehicles due to several unique properties: PLGA-b-PEG copolymers i) are biocompatible and biodegradable and used in many FDA approved products, ii) are capable of encapsulating small- and macro-molecular payloads with a wide range of physiochemical properties, and iii) can be designed for controlled release through a combination of polymer degradation and drug diffusion (Farokhzad O C (2008) *Expert Opin Drug Deliv* 5(9):927-929. The homing to the disease site is driven by the particles' nano-dimensions and PEGylated surface through the enhanced permeability and retention (EPR) effect (Peer, et al., *Nat Nanotechnol* 2(12): 751-760 (2007)).

IV. Methods of Using

The nanoparticles disclosed herein can be delivered in a pharmaceutical compositions using method well known in the art. Pharmaceutical compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In certain embodiments, the compositions are administered systemically, for example, by intravenous or intraperitoneal administration, in an amount effective for delivery of the compositions to targeted cells. Other possible routes include trans-dermal or oral.

In certain embodiments, the compositions are administered locally, for example by injection directly into a site to be treated. In some embodiments, the compositions are injected or otherwise administered directly to one or more tumors. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Harwood Ltd., 1987), which can effect a sustained release of the nanoparticles to the immediate area of the implant.

The nanoparticles can be provided to the cell either directly, such as by contacting it with the cell, or indirectly, such as through the action of any biological process. For example, the nanoparticles can be formulated in a physiologically acceptable carrier or vehicle, and injected into a tissue or fluid surrounding the cell. The nanoparticles can cross the cell membrane by simple diffusion, endocytosis, or by any active or passive transport mechanism.

A. Dosage Forms i. Formulations for Parenteral Administration

In one embodiment the nanoparticles are administered in an aqueous solution, by parenteral injection. The formulation can be in the form of a suspension or emulsion. In general, pharmaceutical compositions are provided including effective amounts of one or more active agents optionally include pharmaceutically acceptable diluents, preservatives, solubilizers, emulsifiers, adjuvants and/or carriers. Such compositions can include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles include, but are not limited to, propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

ii. Formulations for Topical and Mucosal Administration

The nanoparticles can be applied topically. Topical administration can include application to the lungs, nasal, oral (sublingual, buccal), vaginal, or rectal mucosa. These methods of administration can be made effective by formulating the shell with transdermal or mucosal transport elements. For transdermal delivery such elements may include chemical enhancers or physical enhancers such as electroporation or microneedle delivery. For mucosal delivery, PEGylation of the outer shell or addition of chitosan or other mucosal permeants or PH protective elements may be utilized for mucosal delivery.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets, capsules, or lozenges. Oral formulations may include excipients or other modifications to the particle which can confer enteric protection or enhanced delivery through the GI tract, including the intestinal epithelia and mucosa (see Samstein, et al. *Biomaterials,* 29(6): 703-8 (2008).

Transdermal formulations may also be prepared. These will typically be ointments, lotions, sprays, or patches, all of which can be prepared using standard technology. Transdermal formulations can include penetration enhancers. Chemical enhancers and physical methods including electroporation and microneedles can work in conjunction with this method.

B. Disorders to be Treated

The nanoparticles can be targeted to sites of, or associated with, inflammation caused by a disease, disorder; trauma, chemotherapy or radiation. The nanoparticles can provide a selective means of treating inflammatory conditions, where the nanoparticles are targeted to the inflamed tissue to reduce inflammation and enhance resolution.

Representative inflammatory disorders include cardiovascular disorders such as atherosclerosis and ischemia, gastrointestinal disorders such as inflammatory bowel disease, cancer especially after treatment with biological and chemotherapeutic agents that selectively kill cells, thereby releasing cytokine calling in inflammatory cells to clear the necrotic tissue, and autoimmune diseases. Representative autoimmune and/or inflammatory diseases include Alzheimer's disease, Enclosing spondylitis, arthritis (osteoarthritis, rheumatoid arthritis (RA), psoriatic arthritis), asthma, Atherosclerosis, Cohn's disease, colitis, dermatitis, diverticulitis, fibromyalgia, Hepatitis, Irritable bowel syndrome (IBS), systemic lupus erythematous (SLE), nephritis, Parkinson's disease, and ulcerative colitis. A disorder where inflammation plays a major role in long term damage includes reperfusion of tissues and grafts and traumatic brain injury.

Other conditions where excessive inflammation and failed resolution of the inflammatory response are underlying components include cardiovascular disease, obesity-related insulin resistance, scarring, allergic reaction, chronic lung disorders, ischemis (stroke and traumatic brain injury), neurodegenerative disease, and cancer.

Insulin resistance and nonalcoholic steatohepatitis (NASH), characterized by hepatic steatosis combined with inflammation, are major sequelae of obesity. Currently, lifestyle modification (i.e., weight loss) is the first-line therapy for NASH. However, weight loss resolves steatosis but not inflammation. Resolvin D1 (RvD1), an anti-inflammatory and proresolving molecule, has been used to promote the resolution initiated by calorie restriction in obese mice with NASH. Calorie restriction reduced adipose and liver weight (−56 and −13%, respectively; P<0.001), serum leptin and resistin levels, hepatic steatosis, and insulin resistance. Mice receiving RvD1 during the dietary intervention showed increased adiponectin expression at both the mRNA and protein levels and reduced liver macrophage infiltration (−15%, P<0.01). Moreover, RvD1 skewed macrophages from an M1- to an M2-like anti-inflammatory phenotype, induced a specific hepatic miRNA signature (i.e., miR-219-5p and miR-199a-5p), and reduced inflammatory adipokine mRNA and protein expression and macrophage innate immune response. RvD1 attenuated hypoxia-induced mRNA and protein expression of COX-2, IL-1β, IL-6, symptoms of the disease or disorder to be treated.

Typically, the nanoparticles will be administered by injection, intravenously, subcutaneously, intraperitoneally, by infiltration, topically or mucosally (intranasal and CCR7. See Rius, et al. FASEB J. 2014 February; 28(2):836-48 Epub 2013 Nov. 18.

B. Dosages, Dosing Regimens, Route of Administration

The nanoparticles are administered via a route and in an amount effective to alleviate one or more, buccal, rectal, vaginal, pulmonary).

The dosage will be determined in part based on the known pharmacokinetics of the therapeutic and/or diagnostic agent, in combination with animal studies and clinical trials. Such determinations are routine to those skilled in the art.

The present invention will be further understood by reference to the following non-limiting examples.

Example 1: Preparation of Targeted Biodegradable Polymeric NPs Capable of Releasing the Anti-Inflammatory Annexin A1/Lipocortin A1 Mimetic Peptide Ac2-26

Ac2-26 was encapsulated in targeted polymeric NPs in order to improve the pharmaceutical and pharmacological properties of Ac2-26 by enhancing its systemic circulation in vivo; site specific delivery; and controlled release in a spatiotemporal manner. A collagen IV (Col IV)-targeted heptapeptide ligand (Chan, et al. *Proc Natl Acad Sci USA* 107(5):2213-2218 (2010)) was used since Col IV represents 50% of the vascular basement membrane, and it was expected that Col IV exposure will occur at sites of vascular inflammation and injury (Chan et al. *Proc Natl Acad Sci USA* 107(5):2213-2218 (2010); Kalluri, et al *Nature reviews. Cancer* 3(6):422-433 (2003)), enabling targeting of the NPs to sites of vascular injury.

Materials and Methods.
Materials

Ac2-26 peptide was purchased from Tocris Biosciences (Bristol, UK). Zymosan A was purchased from Sigma-Aldrich (St. Louis, Mo.). Alexa Fluor 647 Cadaverine (disodium salt) FITC-Annexin-V were purchased from Invitrogen (Carlsbad, Calif.). The Col IV targeting peptide sequence KLWVLPKGGGC (SEQ ID NO:3), and the scrambled Ac2-26 sequence peptide (Ac-EQWYQN-TEEVSAAFQKVVKEEMIFL-OH) (SEQ ID NO: 4) were purchased from Mimotopes (Victoria, Australia). Carboxy terminated PLGA (50:50 Poly(DL-lactide-co-glycolide), (0.55-0.75 dL/g)) was purchased from Lactel, Adsorbable Polymers. Heterobifunctional PEG polymers; $NH_2$-PEG-COOH and HO-PEG-Maleimide (MW approximately 3400) were purchased from LaysanBio Inc (Arab, Ala.). 1-ethyl-3-(3-dimethylaminopropyl)carbodiimide hydrochloride (EDC), N-hydroxysuccinimide (NHS), N,N-diisopropylethylamine (DIEA) and all other solvents and chemicals were purchased from Sigma-Aldrich (St. Louis, Mo.). $^1$H NMR spectra were recorded on a Bruker AVANCED-400 NMR spectrometer. Ac2-26 quantification measurements were carried out on a Nanodrop UV-Vis spectrometer. Peptide-encapsulated NPs were prepared using the nanoprecipitation method. The NP sizes and zeta potentials were obtained by quasi-electric laser light scattering using a ZetaPALS dynamic light-scattering detector (15 mW laser, incident beam ¼ 676 nm; Brookhaven Instruments). Electron microscopy (EM) was performed at the Harvard Medical School EM facility on a Tecnai™ $G^2$ Spirit BioTWIN EM.

Methods
Synthesis of Di and Triblock Polymers.

In order to formulate polymeric nanoparticles, di and triblock copolymers of poly(lactic-co-glycolic acid-b-polyethyleneglycol) PLGA-PEG and triblock PLGA-PEG-collagen IV targeted polymers and a fluorescent polymer were synthesized according to FIGS. 2A-D.

The carboxy terminal of PLGA and the amino functionality of PEG were coupled using 1-ethyl-3-(3-dimethylaminopropyl)carbodiimide hydrochloride (EDC) and N-hydroxysuccinimide (NHS) activation methodology (FIG. 2A). A fluorescent polymer was also synthesized by coupling carboxy terminated PLGA to Alexa 647 Cadaverine (FIG. 2B). The KLWVLPK (SEQ ID NO: 5) peptide was initially coupled to PEG via the free thiol of the C-terminal GGGC (SEQ ID NO: 6) linker using maleimide chemistry, purified, and subsequently coupled to PLGA carboxy using a similar EDC/NHS coupling chemistry used to form the diblock PLGA-PEG (FIG. 2C).

Synthesis of PLGA-PEG-COOH (FIG. 2A)

Dry DCM (1 mL) was added to 50:50 Poly(DL-lactide-co-glycolide) (0.55-0.75 dL/g) (100 mg, 0.0023 mmol) and to this was added EDC (4.41 mg, 0.023 mmol) dissolved in dry DCM (0.5 mL), and the reaction stirred for 10 min. Subsequently NHS (2.65 mg, 0.023) was dissolved in dry DCM (0.5 mL) and added to the reaction and the reaction was left to stir at RT for 60 min. The solution was then added dropwise into 1 Methanol (50 mL) and the resultant precipitate was centrifuged (3000 rpm, 5 min), and the supernatant decanted, the pellet dissolved in DCM (1 mL) and then further washed (×2). The pellet was then dried under vacuum for 90 min after which it was dissolved in dry $CHCl_3$ (1 mL). To this was added heterobifunctional $NH_2$—PEG-COOH (9.52 mg, 0.0028 mmol) dissolved in dry $CHCl_3$ (0.5 mL), followed by the addition of DIEA (3.62 mg, 0.028 mmol), and the reaction stirred for 12 h at RT. The copolymer was then precipitated by dropwise addition into cold diethylether/methanol (15:35 mL) and centrifuged (3000 rpm, 5 min). The supernatant was decanted and the pellet redissolved in $CHCl_3$ (1 mL), precipitated and washed further (×3) and dried under vacuum to yield PLGA-PEG-COOH (1) (yield 80%). $^1$H NMR (400 MHz, $CDCl_3$): ä 5.22 (m, (—OC$\underline{H}$($CH_3$)CONH—), 4.82 (m, (—OC$\underline{H}_2$COO—), 3.63 (s, (—C$\underline{H}_2$C$\underline{H}_2$O—), 1.58 (d, (—OCH(C$\underline{H}_3$)CONH—) ppm.

Synthesis of PLGA-PEG-Mal (FIG. 2B)

The PLGA-PEG-COOH diblock polymer 1 (100 mg, 0.0021 mmol) was dissolved in DCM (1 mL) and to this was added EDC (4.03 mg, 0.021 mmol) in dry DCM (0.5 mL) and the reaction stirred for 10 min. Subsequently NHS (2.42 mg, 0.021) was dissolved in dry DCM (0.5 mL) and added to the reaction. The reaction was left to stir at RT for 60 min. The solution was then added drop wise into Methanol (50 mL) and the resultant precipitate was centrifuged (3000 rpm, 5 min), and the supernatant decanted, the pellet was dissolved in DCM (1 mL) and then further washed (×2). The pellet was then dried under vacuum for 90 min after which it was dissolved in dry $CHCl_3$ (1 mL) To this was then added heterobifunctional HO-PEG-maleimide (8.84 mg, 0.0026 mmol) dissolved in dry CHCl$_3$ (0.5 mL), followed by DIEA (3.36 mg, 0.026 mmol) and the reaction stirred for 12 h at RT. The copolymer was then precipitated by drop wise addition into cold diethylether/methanol (15:35 mL) and centrifuged (3000 rpm, 5 min). The supernatant was decanted and the pellet redissolved in CHCl$_3$ (1 mL), precipitated and washed further (×3) and dried under vacuum to yield PLGA-PEG-Mal (2) (yield 65%). $^1$H NMR (400 MHz, CDCl$_3$): ä 6.69 (—HC═CH—), 5.20 (m, (—OCH(CH$_3$)COO—), 4.80 (m, (—OCH$_2$COO—), 4.27 (—NCH$_2$CH$_2$—), 3.64 (s, (—CH$_2$CH$_2$O—), 2.5 (—NCH$_2$CH$_2$—CONH—), 1.56 (—OCH(CH$_3$)CONH—) ppm.

Synthesis of PLGA-PEG-Col IV Targeting Polymer

The Col IV targeting peptide sequence (H-KLWVLPK-GGGC-NH$_2$ (SEQ ID NO: 3), 2.36 mg, 0.002 mmol), which was previously dissolved in dry DMF (1 mL), was added to the synthesized PLGA-PEG-Mal 2 (81.7 mg, 0.0017 mmol) dissolved in dry DMF (1 mL). To this was added Et$_3$N (2.31 mg, 0.002 mmol) and the reaction stirred at RT for 24 h. The solution was then added drop wise into cold Methanol (100 mL) and the resultant precipitate was centrifuged (3000 rpm, 5 min), the supernatant decanted, and the pellet was further washed (×3). The pellet was then dried under vacuum to yield 3 (FIG. 2C) (yield 67%). $^1$H NMR (400 MHz, CDCl$_3$): ä PLGA-PEG-Mal: 5.21 (m, (—OCH(CH$_3$)COO—), 4.82 (m, (—OCH$_2$COO—), 4.29 (—NCH$_2$CH$_2$—), 3.64 (s, (—CH$_2$CH$_2$O—), 1.58 (—OCH(CH$_3$)CONH—), peptide peaks: 8.02 (sharp s), 7.52, (s) 7.44-7.8 (m), 7.22-7.06 (m), 6.93-6.69 (m), 4.99 (s), 4.9-4.59 (m), 4.30 (m), 3.78-3.73 (m), 2.17 (s), 1.8-1.45 (m), 1.4-1.17 (m), 0.9-0.77 (m) ppm.

Synthesis of PLGA-Alexa 647

Figure 2D:
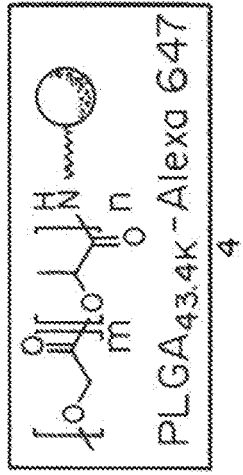
FIGS. 2A-2C is a schematic of polymer synthesis. The diblock PLGA-PEG polymer is synthesized by first activating the carboxy distal end of 50:50 Poly(DL-lactide-co-glycolide) with 1-ethyl-3-(3-dimethylaminopropyl)carbodi-imide hydrochloride (EDC) and N-hydroxysuccinimide (NHS) conjugation crosslinkers in DCM, followed by conjugation with the heterobifunctional $NH_2$-PEG-COOH in the presence of N,N-diisopropylethylamine (DIEA) to yield 1 (FIG. 2A). The Col IV peptide conjugated targeting polymer (PLGA-PEG-Col IV) (FIG. 2C) is synthesized by initially coupling the heterobifunctional HO-PEG-maleimide to PLGA in order to form an ester bond to eventually yield PLGA-PEG-Mal.
Figure 2D:
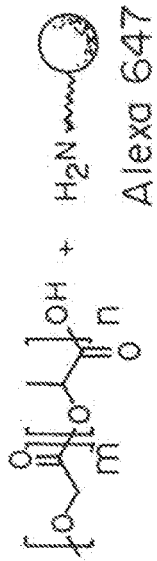

Dry DCM (1 mL) was added to 50:50 Poly(DL-lactide-co-glycolide) (0.55-0.75 dL/g) (100 mg, 0.0023 mmol) and to this was added EDC (4.41 mg, 0.023 mmol) in dry DCM (0.5 mL) and the reaction stirred for 10 min. Subsequently NHS (2.65 mg, 0.023) was dissolved in dry DCM (0.5 mL) and added. The reaction was left to stir at room temperature (RT) for 60 min. The PLGA-NHS activated polymer was precipitated with 20 mL of cold 1:1 Methanol/Ethanol mixture and centrifuged at 2700×g for 10 min to remove residual EDC/NHS. The washing and centrifugation steps were repeated twice, and the polymer was then dried under vacuum for 90 min to remove residual solvents. After drying, PLGA-NHS was dissolved in DCM (1 mL) followed by the addition of Alexa 647 cadaverine (3.50 mg, 0.0028 mmol) dissolved in dry DCM (0.5 mL), followed by DIEA (3.62 mg, 0.028 mmol) and the reaction stirred for 12 h at RT. The polymer was then precipitated with 20 mL of cold 1:1 Methanol/Ethanol mixture and centrifuged at 2700×g for 10 min. The washing was repeated twice more and the product dried under vacuum (obtained a blue polymer compound). The supernatant was decanted and the pellet redissolved in CHCl$_3$, precipitated and washed further (×3) and dried under vacuum to yield 4 (yield 95%) (FIG. 2D). $^1$H NMR (400 MHz, CDCl$_3$): ä PLGA peaks: 5.21 (m, (—OCH(CH$_3$)CONH—), 4.83 (m, (—OCH$_2$COO—), 1.59 (d, (—OCH(CH$_3$)CONH—) ppm.

With the polymers in hand, the NPs were formulated, purified, and characterized.

Formulation and Characterization of NPs.

The NPs were formulated via a single step nanoprecipitation self-assembly method. The synthesized polymers and Act-26 peptide were dissolved in acetonitrile (total polymer 3 mg/mL), and 2% (wt/wt) of the fluorescent PLGA-Alexa 647 was added to all formulations. All formulations contained 4% (wt/wt) peptide (either Ac2-26 or scrambled Ac2-26) and targeted formulations contained 5% (wt/wt) of the triblock collagen IV targeting polymer. The organic mixture containing the polymers and peptide was then added dropwise to nuclease free water (10 mL) The solution was stirred for 2-4 h and the particles were filtered, washed and resuspended in water or PBS.

Specifically, the required polymers (3.12 mg/mL, 3 mg polymer+120 μg Ac2-26 peptide) and Ac2-26 or scrambled Ac2-26 (0.12 mg/mL) were dissolved in acetonitrile. The polymer/peptide mixture was then added dropwise to 10 mL of nuclease free water. The solution was stirred for 2 h and the particles were filtered through sterile 0.45 μm syringe filters (regenerated cellulose, 17 mm, Cole Palmer Instruments). The NPs were concentrated by centrifugation at 3000×g for 20 min using Amicon Ultra-15 centrifugal filter units (molecular weight cut off, "MW CO", 100 KDa, Sigma-Aldrich), washed with deionized water, and resuspended in 1 mL of either nuclease free H$_2$O or phosphate buffered saline, "PBS" (total 3.12 mg/mL NP).

For in vivo studies, NPs were resuspended in 1 mL of H$_2$O (total 3.12 mg/mL NP) and then further diluted with PBS prior to injection. The NPs were diluted twenty-fold in either H$_2$O or PBS, and their size and surface charge measured using dynamic light scattering.

For Transmission electron microscopy (TEM), a 10 μL solution of 1 mg/mL freshly prepared NPs in H$_2$O was deposited on carbon coated copper grids, the excess solution was blotted, and the grids were immersed in a solution of 0.75% uranyl formate stain. The stain was blotted, and the dried grids imaged within 1 h of preparation on a TECNAI™ G$^2$ Spirit BioTWIN electron microscope equipped with an AMT 2 k CCD camera and low-dose software (80 kV, direct mag. 98000×). A calibration curve of various concentrations of the Ac2-26 or scrambled Ac2-26 peptide was also generated in order to quantify the amount of peptide retained in the NP formulations. The absorbance of the initial filtrate was measured at 220 nm, and the % encapsulation efficiency and % loading of the peptides were calculated.

Figure 1B:
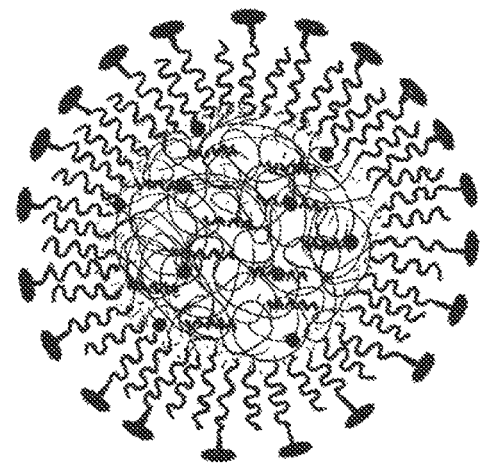
Figure 1C:
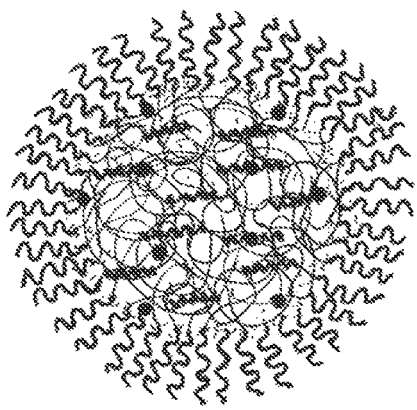
Figure 1D:
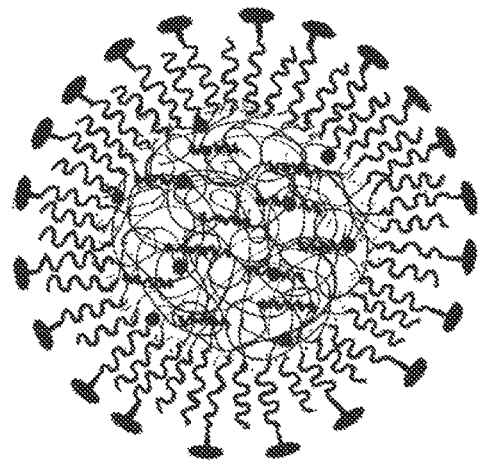

In addition to Ac2-26 NPs (FIG. 1A) and targeted Ac2-26 NPs (FIG. 1B), control targeted (FIG. 1D) and non-targeted (FIG. 1C) NPs containing an isoelectric miss-matched scrambled (Scrm) sequence were also formulated for comparison.

The peptide loading and release rates of peptides from the NPs were then measured.

Ac2-26 NP Release Kinetics Study.

The release kinetics of Ac2-26 from targeted and non-targeted NPs was measured by incubating the NPs at 37° C. and then measuring the released peptide in solution, which was isolated via ultracentrifugation. Released peptide concentrations were measured using UV-spectroscopy, and a cumulative release curve was generated Specifically, 3 mg/mL NP samples were formulated in PBS, and the NPs were incubated in Eppendorfs in triplicate at 37° C. At defined time intervals (8, 24, 48, 72 and 96 h), the NPs were removed, transferred to Amicon Ultra-15 centrifugal filter units (MW CO 10 KDa, Sigma-Aldrich), and centrifuged at 3000×g for 20 min. The NPs were then resuspended in PBS and then incubation was continued until the designated time point. The filtrate (10 μL) was analyzed with a nanodrop UV-vis spectrometer, and absorbance was measured at 220 nm in order to determine the amount of released peptide at each time point.

Results

Figure 3A:
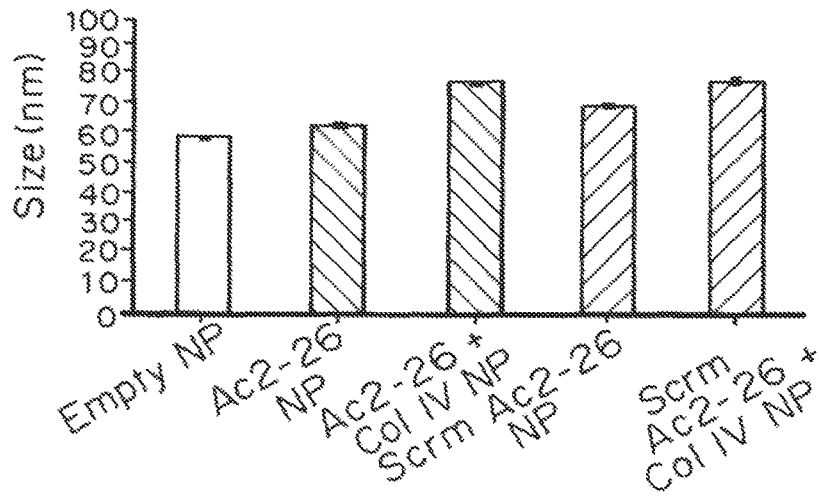
FIGS. 3A-3C are graphs showing the dynamic size (nm) (3A), charge (mV) (FIG. 3B), and % loading (FIG. 3C) of the NPs.

The hydrodynamic size of the various NPs in water were as follows:
- empty NPs, 58.1±0.8 nm;
- Ac2-26 NPs, 62.1±0.8 nm;
- Ac2-26 Col IV NPs, 76.3±0.9 nm;
- Scrm Ac2-26 NPs, 68.4±0.7 nm; and S
- Scrm Ac2-26 Col IV NPs, 77.15±1.1 nm (FIG. 3A). FIG. 3A shows dynamic light scattering measurements of empty, non-targeted (Ac2-26 NP), targeted (Ac2-26+Col IV NP), scrambled peptide (Scrm Ac2-26 NP), and targeted scrambled peptide (Scrm Ac2-26+Col IV NP) formulations were measured (mean±SD, n=3).

Figure 3B:
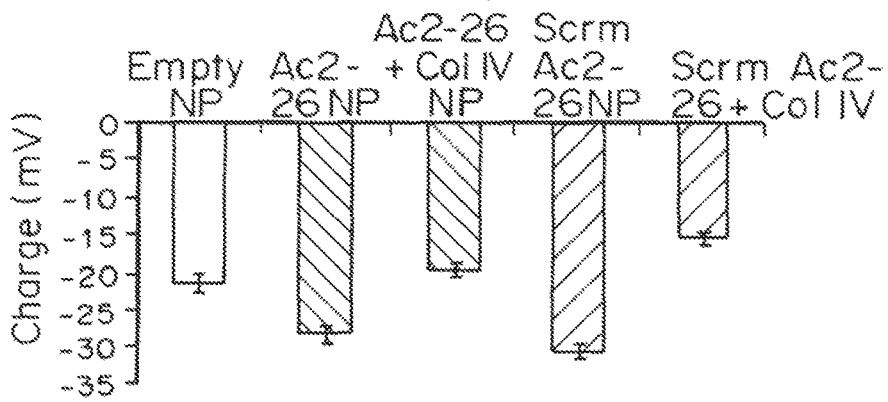

The surface charge of the NPs were as follows:
- empty NPs, −21.55±1.21 mV;
- Ac2-26 NPs, −28.77±0.82 mV;
- Ac2-26 Col IV NPs, −19.68±0.78 mV;
- Scrm Ac2-26 NPs, −30.71±1.0 mV; and
- Scrm Ac2-26 Col IV NPs, −15.49±0.84 mV (FIG. 3B). FIG. 3B shows the Zeta potential of the formulations.

The Col IV-bearing formulations were larger than the non-targeted NPs (approximately 8.75 nm for Ac2-26 Col IV NPs and approximately 14.2 nm for Scrm Ac2-26 Col IV NPs) and were also more positive in charge (approximately 9.09 mV and approximately 15.22 mV, respectively). The increase in size is attributed to the increased bulk of the NPs bearing the Col IV targeted peptide sequence and the increase in positive charge may be due to the N-terminal exposed orientation of the peptide.

The loading of the peptide in the NPs was optimal up to 4% nominal loading (peptide/polymer wt/wt). At this ratio the NPs were stable, and release could be optimally tuned. The size of the NPs was also kept at sub-100 nm for improved vessel adhesion and retention.

The percent encapsulation efficiency (EE) and loading were measured to be approximately 90% and 3.36%, respectively, for peptide-loaded NPs. The Ac2-26 NPs were optimized for sustained release, i.e., up to a period no longer than one week, in order to facilitate a single weekly dosing regimen for future studies using chronic inflammatory disease models.

Figure 3C:
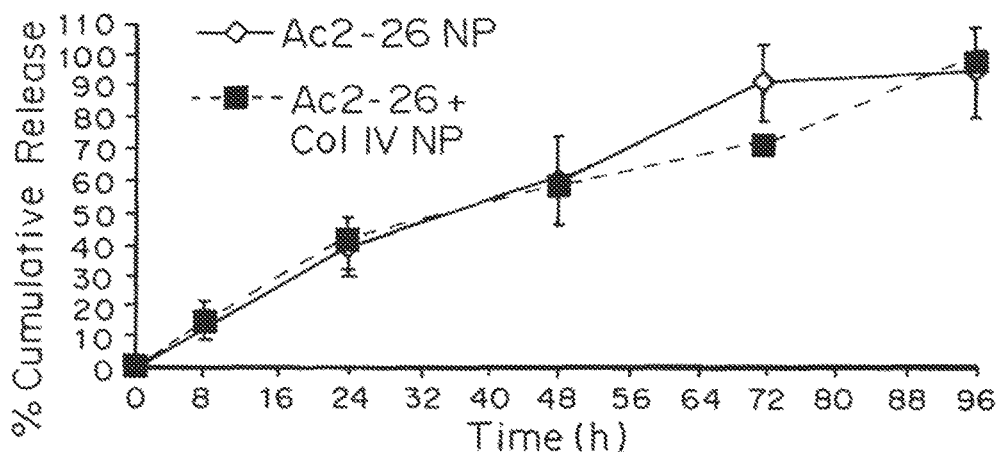

The release kinetics of Ac2-26 from targeted and non-targeted NPs was is shown as a cumulative release curve in FIG. 3C. The release of Ac2-26 from the NPs was found to be approximately 20% per day. Transmission electron microscopy (TEM) revealed that the targeted NPs were spherical and had uniform structure.

Example 2: Blockade of Zymosan-Stimulated Polymorphonuclear (PMN) Leucocyte Recruitment in an Acute Peritonitis Model A model of self-limited peritonitis was used to quantitatively assess resolution in vivo to determine whether the developed NPs containing Ac2-26 are anti-inflammatory and/or pro-resolving (Bannenberg 2005; Schwab 2007). Zymosan A was administered to C57BL/6J mice. In parallel, mice were then given vehicle, empty NPs as control, Ac2-26 in NPs, Scrm Ac2-26 in NPs, Ac2-26 native peptides described in detail below. Equal polymer concentration was loaded in both the NPs and Ac2-26 NPs.

Materials and Methods

NPs were prepared as described in Example 1.

In Vivo Murine Peritonitis.

1 ml of zymosan A (100 µg/mouse) in 1 ml of sterile saline was administered to female C57BL/6J mice (6-8 wk old, Charles River Laboratories, Wilmington, Mass., USA) to induce peritonitis (Bannenberg et al. *J Immunol* 174(7): 4345-4355 (2005); Norling, et al. (2011) *J Immunol* 186 (10):5543-5547). Zymosan (100 µg/mouse) was administered intraperitoneally (i.p.) to each mouse. The mice were divided into four groups and received intravenous (i.v.) injections of Vehicle (empty nanoparticles (NPs)); NPs containing Ac2-26 (Ac2-26 NP, 100 ng/mouse); scrambled Ac2-26 (Scrm NP, 100 ng/mouse), or Ac2-26 native peptide (100 ng/mouse).

For baseline PMN number measurements, mice were euthanized at selected time intervals (4, 12, or 24 hours post zymosan stimulation), with an overdose of isofluorane, following which peritoneal exudates were collected by lavaging with $Ca^{2+}/Mg^{2+}$ free phosphate buffered saline ($PBS^{-/-}$, 5 ml). Leukocytes were counted with a hemocytometer.

Peritoneal exudates were harvested 4 h post zymosan initiation, and living cells were quantified using trypan blue exclusion.

Differential cell counts were assessed via flow cytometry using an LSRII flow cytometer. For this analysis, cells were stained with FITC-conjugated rat anti-mouse Ly-6G (clone 1A8) or rat IgG2c, κ isotype control. All procedures were conducted in accordance with protocols approved by the Columbia University Standing Committee on Animals guidelines for animal care.

Statistical Analysis.

Student's t-test or one-way ANOVA with post-hoc Tukey tests were used to determine significance. All error bars represent S.E.M.

Results

The results demonstrate that Act-26 NPs are pro-resolving in vivo and are significantly more potent than the Ac2-26 native peptide at blocking zymosan-stimulated PMN recruitment in an acute peritonitis model.

Figure 4A:
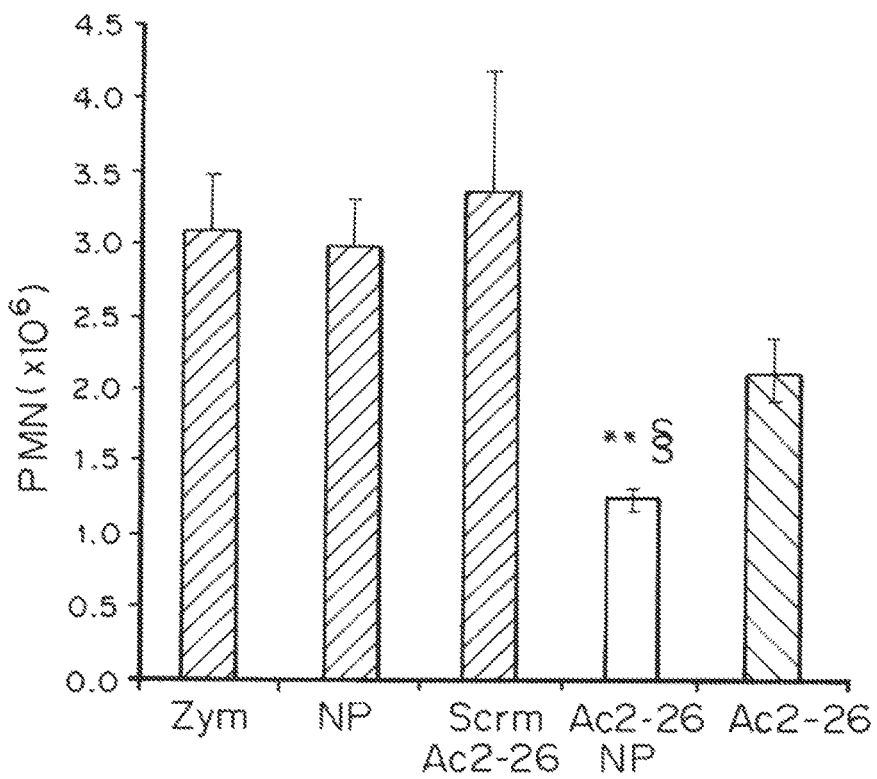
FIGS. 4A-C shows the effect of Ac2-26 NPs on polymorphonuclear neutrophils (PMN), in vivo.

Ac2-26 NPs blocked zymosan-stimulated PMN infiltration by approximately 56% (p<0.01), whereas freely administered Ac2-26 peptide blocked PMN infiltration by only approximately 30%, which did not reach statistical significance (FIG. 4A). Empty NPs did not exert a protective effect, indicating that the pro-resolving action was as a result of the Ac2-26 and not from the polymeric composition of the NPs. The Ac2-26 scrambled peptide was also not protective, confirming that the specific sequence of Ac2-26 peptide confers protective action (FIG. 4A).

Flow cytometric analysis of the peritoneal exudate cells showed that there were less PMNs in the Ac2-26 NP-treated group versus the zymosan-alone group.

Figure 4B:
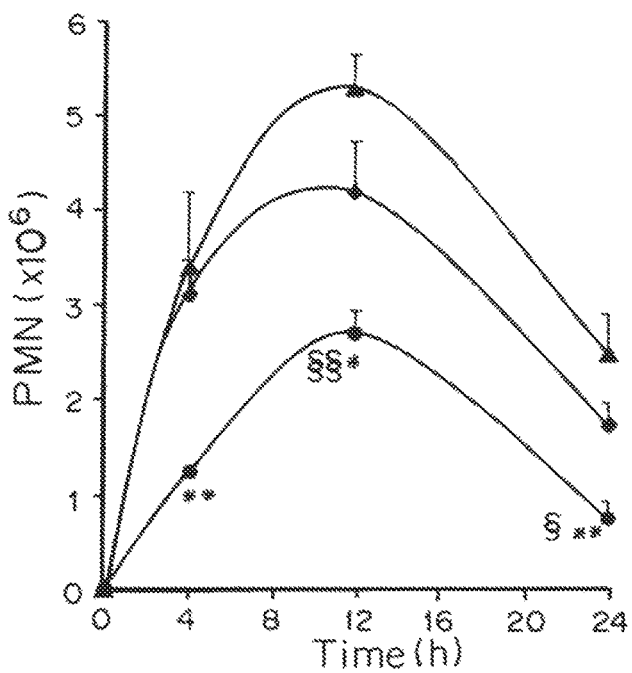
Figure 4C:
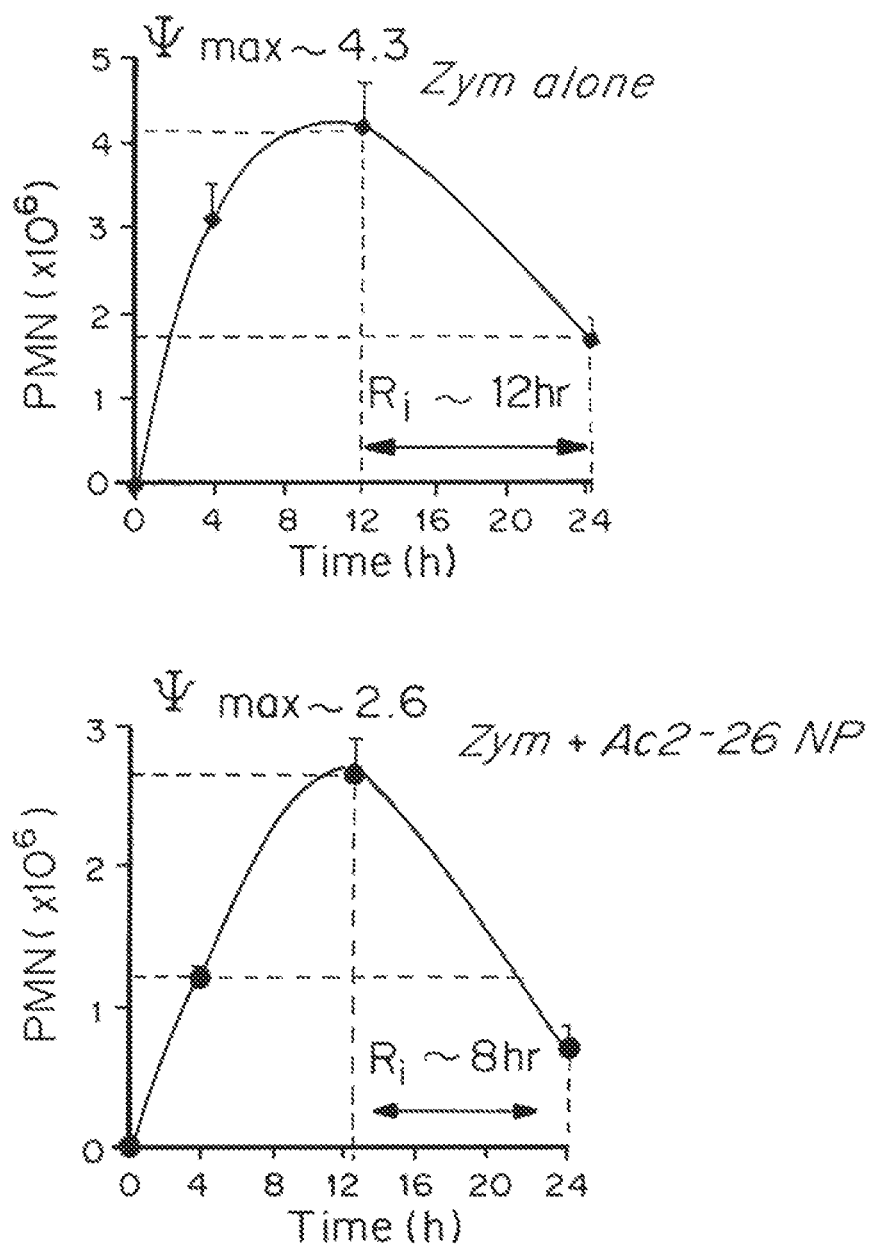

Acute inflammation and its timely resolution are programmed temporal events (Serhan, et al. (2007) *FASEB J* 21(2):325-332). In this regard, resolution can be defined at the histological level as the interval from maximum PMN infiltration to the point where they are lost from the tissue (Bannenberg et al. *J Immunol* 174(7):4345-4355 (2005). Zymosan exhibited a self-limited PMN curve with a maximal PMN infiltration (ψmax) of approximately $4.3 \times 10^6$ PMNs, a $T_{max}$ of 12 h (FIG. 4B), and a resolution interval ($R_i$) of ~12 h (FIG. 4C). The scrambled Ac2-26 peptide did not block zymosan-stimulated PMN infiltration at any time point. In contrast, NPs containing Ac2-26 significantly blocked PMN infiltration at 4, 12 and 24 h post-zymosan challenge and exhibited a ψ max of ~$2.6 \times 10^6$ PMNs (a $T_{max}$ of 12 h (FIG. 4B), and a $R_i$ of 8 h (FIG. 4C).

Thus, Ac2-26 NPs (100 ng/mouse) enhanced resolution 4 h faster than zymosan alone.

Example 3: Reduction of Ischemia Reperfusion Injury

Excessive accumulation of PMN within tissues can lead to tissue damage, amplification and prolongation of the inflammatory response (Majno & Joris, *Cells, tissues, and disease: principles of general pathology* (Oxford University Press, New York) 2nd Ed pp xxviii, 1005 (2004)). Since Ac2-26 NPs limits PMN infiltration in vivo the actions of Ac2-26 NPs in a model of tissue injury driven by excessive PMN infiltration and activation was examined (Qiu et al. *Proc Natl Acad Sci USA* 97(8):4267-4272).

Col IV is abundant in basement membranes and is exposed upon injury. It was hypothesized that the targeted NPs would home to the site of injury and release Ac2-26 more efficiently than the non-targeted NPs.

Materials and Methods

NPs were prepared as described in example 1.

Hind-Limb Ischemia Reperfusion Injury.

Hind-limb ischemia was induced by placing a tourniquet around the hind limb for 1 h, as described by Qiu, et al., *Proc Natl Acad Sci USA* 97(8):4267-427 (2000). Reperfusion was carried out for 1 h.

At the time of reperfusion, mice were administered 1 µg i.v. of either Col-IV targeted Ac2-26 NPs, Ac2-26 NPs, Col IV-targeted scrambled Ac2-26 NPs, or vehicle alone. After one hour of reperfusion, the mice were euthanized, and the gastrocnemius muscle was harvested and placed in cold lysis buffer and homogenized. The gastroconemius muscle tissue was harvested, lysed and homogenized. Tissue levels of myeloperoxidase (MPO) in the resulting supernatants were determined using a mouse MPO enzyme-linked immunosorbent assay (Hycult biotechnology, Cell Sciences, Uden, The Netherlands).

Results

The results show that Col IV targeted Act-26 NPs exert a tissue-restorative property in a hind limb ischemia-reperfusion model of vascular and tissue injury.

Figure 5:
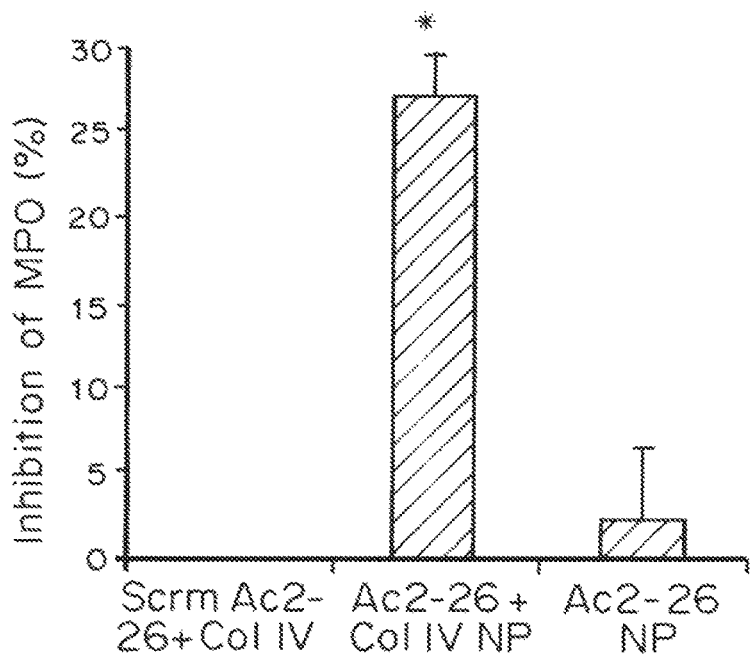
FIG. 5 is a graph of the percent inhibition of Col-IV-targeted Ac2-26 NPs limit PMN infiltration into injured tissue. (n=3/treatment mean±SEM). The data are plotted as inhibition of tissue MPO. *p<0.05 Col-IV for Ac2-26 NPs vs. Ac2-26 NPs or vs. Scrm Ac2-26 Col-IV targeted NPs.

Ac2-26 Col IV NPs differentially localized to the injured tissue. By contrast, the non-targeted Ac2-26 NPs did not differentially localize to the injured tissue. Also, Ac2-26 Col IV NPs limited PMN infiltration by approximately 30%, whereas Ac2-26 NPs or Scrm Ac2-26 Col-IV NPs had none or little inhibitory effect (FIG. 5). Thus, Ac2-26 Col IV NPs displayed a restorative action in this model of tissue injury after just 1 h post systemic administration.

The results demonstrate that Ac2-26 NPs can be encapsulated successfully in sub-100 nm NPs; exhibit controlled temporal release; and exert potent pro-resolving actions in vivo, indicating that they enhance endogenous resolution programs. Encapsulation of Ac2-26 allowed use of much lower doses of Ac2-26 than has been shown in the prior art, to protect against ischemia reperfusion injury. Specifically, the studies by La, et al. *FASEB J* 15(12):2247-2256 (2001) and Facio, et al. *J Mol Med (Berl)* 89(1):51-63 (2011) of protective effect of Ac2-26 in myocardial and renal ischemia reperfusion injury, respectively, used Ac2-26 at a much higher µg dose range. By contrast the data disclosed herein shows that Ac2-26 is effective in doses as low as 1 µg/mouse, if encapsulated in NPs. An approximately 30% inhibition of PMN infiltration into the damaged gastrocenemius was observed (FIG. 5). Since PMNs can also have protective and restorative actions in this model, complete inhibition is not desirable, because it would be detrimental to the overall resolution of tissue inflammation, underscoring the fact that tempering acute inflammation (rather than blocking it), is an optimal intervention.

Example 4: Preparation of Nanoparticles Containing a Liver X Receptor Agonist and Drug Release A NP platform to deliver a liver X receptor (LXR) agonist to macrophages in atherosclerotic plaques was developed.

LXR agonists have been shown to be potent anti-inflammatory factors in macrophages and a key factor in the regression of atherosclerosis. LXR activation is involved in the pivotal steps of inflammation resolution by suppressing inflammatory cytokine production, promoting cholesterol efflux from cholesterol-loaded macrophages, and enhancing efferocytosis (Tabis; Feig et al. *J Clin Invest* 120(12):4415-4424). Recent studies have shown that treatment with LXR agonist in a mouse model of atherosclerosis results in attenuation of atherosclerosis in vivo (Joseph, et al. *Proc Natl Acad Sci USA* 99(147604-7609 (2002); Levin, et al. *Arterioscler Thromb Vasc Biol* 25(1):135-142 (2005)).

Phosphatidylserine (PS) is generally considered to be a marker for apoptosis, a key event in the progression of atherosclerosis. PS serves as a surface ligand on apoptotic cells and can be recognized by macrophages (Fadok, et al. *J Immunol* 148(7):2207-2216 (1992)). Using a rat model of acute myocardial infarction (MI), Cohen and co-workers demonstrated the ability of PS-presenting liposomes to prompt the immune system's macrophages to shift to an anti-inflammatory mode, promoting angiogenesis, preventing ventricular remodeling, and eliciting infarct repair (Harel-Adar, et al. *Proc Natl Acad Sci USA* 108(5):1827-1832 (2011).

A peptide or phosphatidylserine (PS) functionalized nanoparticle (NP) platform has been developed to selectively deliver therapeutic compounds such as GW3965 into atherosclerotic plaques for the treatment of atherosclerosis.

To promote resolution of inflammation, a PS lipid was incorporated into PLGA-PEG NPs to form polymer/lipid hybrid NPs. After the incorporation of PS, the resultant hybrid NPs exhibited a decrease in particle size and an increase in drug loading with increasing PS content.

This study examined the utility of a synthetic LXR agonist GW3965, which was encapsulated within polymeric NPs, to inhibit atherogenic progression. Targeted NPs formulated using two peptide-functionalized polymers composed of end-to-end linkages between PLGA-b-PEG and LyP-1 or CREKA, respectively, to further enhance the accumulation of NPs within atherosclerotic plaques.

Ruoslahti and co-workers identified LyP-1 as a 9-amino acid cyclic peptide that can specifically bind to P32 protein on the surface of plaque macrophages (Hamzah, et al. *Proc Natl Acad Sci USA* 108(17):7154-7159 (2011). CREKA-modified micelles have also shown to bind the clotted plasma proteins on the luminal surface of atherosclerotic plaques (Peters, et al. *Proc Natl Acad Sci USA* 106(24): 9815-9819 (2009)). It was hypothesized that functionalization of NPs with LyP-1 or CREKA peptides may be able to facilitate the delivery of GW3965 to atherosclerotic lesions.

Materials and Methods

Peptide functionalized NPs were formulated through self-assembly of a biodegradable triblock copolymer composed of end-to-end linkages between poly(lactic-co-glycolic acid)-poly(ethylene glycol) (PLGA-PEG) and either LyP-1 or CREKA (SEQ ID NO: 1), designated as $TNP_{LyP-1}$ and $TNP_{CREKA}$, respectively. A third nanoformulation was synthesized by incorporating PS into the PLGA-b-PEG NPs. GW3965, a synthetic liver X receptor (LXR) agonist which has been shown to be a potent anti-inflammatory factor in macrophages, was encapsulated within the NPs at high loading efficiencies and sustainably released over 2 weeks.

Figure 6A:
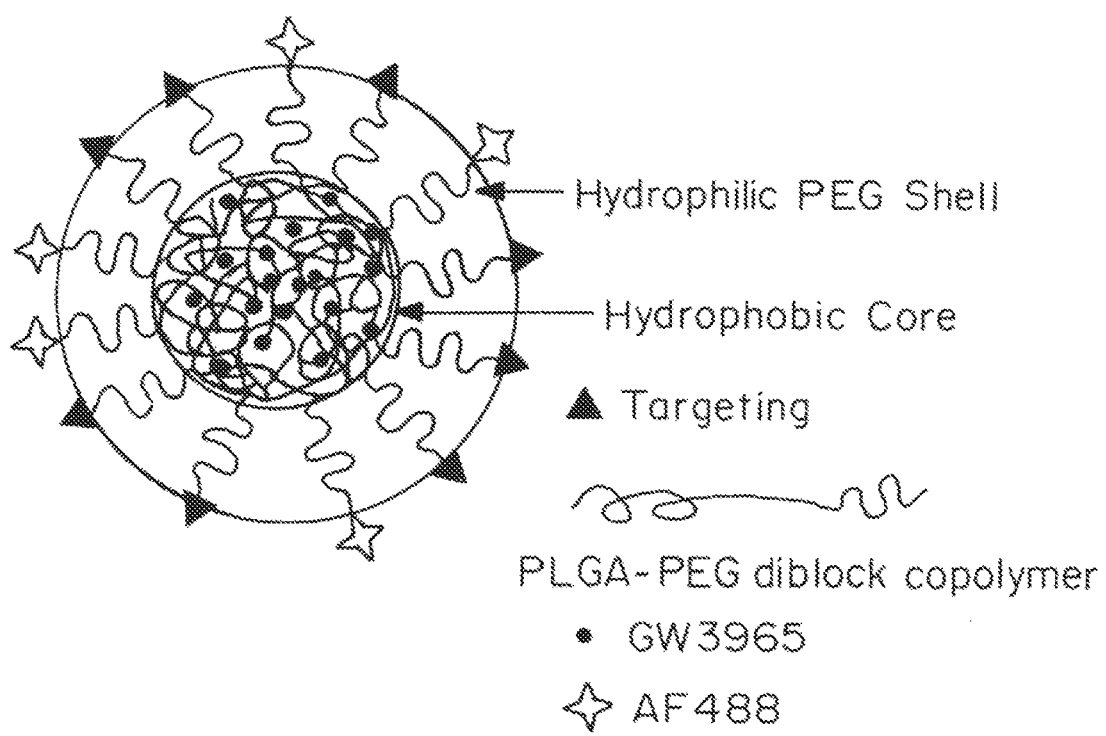
FIG. 6A shows the chemical structure of targeted NPs (TNPs). The particle consists of a hydrophobic core containing LXR agonist, a hydrophilic PEG corona, and a target ligand that can bind to cells or other components within atherosclerotic plaques.

The design and preparation of GW3965-containing NPs are shown in FIG. 6A. NPs were prepared through self-assembly of either PLGA-b-PEG or a mixture of PLGA-b-PEG and the corresponding PLGA-b-PEG-peptide conjugate using a single emulsion-solvent evaporation method. The targeting efficacy of NPs varied with the weight ratio of non-functionalized and ligand-modified polymers. NPs with a fixed polymer/polymer-peptide weight ratio of 39 were used to achieve optimal targeting capabilities and physiochemical properties. NPs formulated using the mixture of PLGA-b-PEG and PLGA-b-PEG-peptide conjugates were designated as either $TNP_{LYP1}$ or $TNP_{CREKA}$, while NPs formulated with PLGA-b-PEG were designated as CNP. LyP-1 was conjugated to PLGA-b-PEG-maleimide via an extra N-terminal cysteine using maleimide-thiol conjugation chemistry. Similarly, CREKA (SEQ ID NO: 1) peptide was conjugated to PLGA-b-PEG-maleimide via an N-terminal cysteine to yield the PLGA-b-PEG-CREKA conjugate.

NPs were characterized by Transmission electron microscopy (TEM) obtained with air-dried NPs stained with uranyl acetate solution To measure drug release kinetics, NP samples were dialyzed against 2 L of frequently renewed PBS at pH 7.4 and 37° C. to mimic physiological conditions. Quadruplicate aliquots of each NP sample (n=4) were withdrawn at indicated time points for RP-HPLC analysis.

Results

As shown in FIG. 6A, the resultant NPs consist of a hydrophobic core containing LXR agonist, a hydrophilic PEG corona, and a target ligand that can bind to macrophages or other components within atherosclerotic plaques.

Figure 6B:
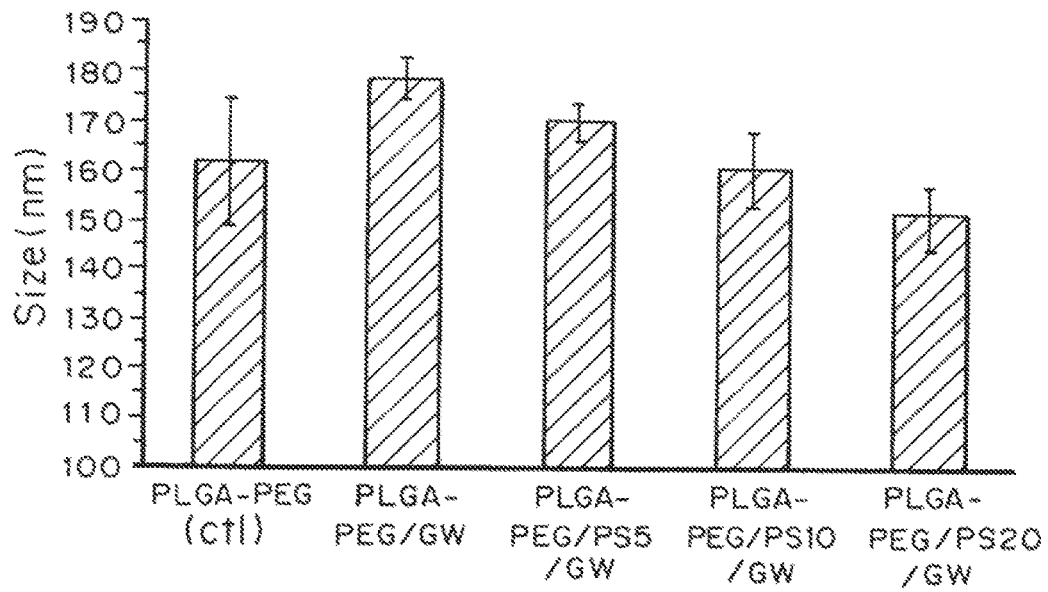
FIG. 6C is a graph of the % loading of the NPs.
Figure 6C:
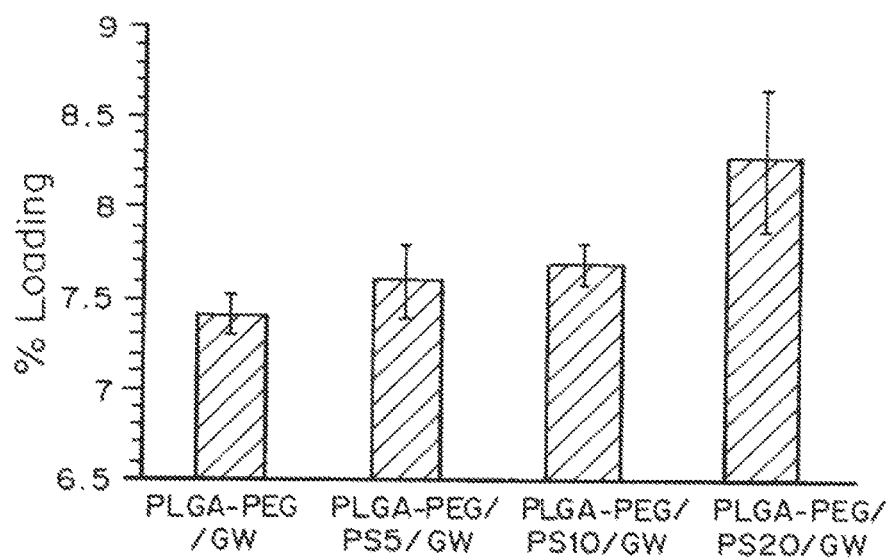

Transmission electron microscopy (TEM) obtained with air-dried NPs stained with uranyl acetate solution showed that the particles were spherical and monodisperse. The sizes of nonfunctionalized NPs measured by dynamic light scattering were found to be 156.6±10.3 nm (mean±SD) with a polydispersity index (PDI) at or lower than 0.21. Peptide attachment resulted in a size increase of approximately 30 nm See FIG. 6B. Calculated based on the drug content by RP-HPLC, the final drug entrapment and loading efficacy using a 20 wt % GW3965/polymer input were determined to be 86.6±1% of the drug input weight and 15.0±0.2% by the drug/polymer weight for CNP, 72.8±4.3% and 12.6±0.7% for $TNP_{LYP-1}$, and 77.4±5.7% and 12.9±0.9% for $TNP_{CREKA}$, respectively (FIG. 6C).

The ability of these GW3965-containing NPs to downregulate the expression of key inflammation related genes and to up-regulate the expression of LXR-responsive genes was investigated both in vitro and in vivo.

In this system, GW3965 compound is homogeneously dispersed by encapsulation throughout the hydrophobic PLGA core and is released through a diffusion-controlled process and polymer degradation. 20.7% of the total GW3965 was rapidly released from CNP over the first 6 hours followed by a sustained release after 8 hours. This controlled release of GW3965 from the CNP extended over 2 weeks, reaching a maximum value of 84.4% thereafter. The release profile of $TNP_{LyP-1}$ showed that the peptide conjugation slightly interfered with the self-assembly process to marginally increased rates of drug release. The drug release reached a maximum value of 98.5% over 14 days and the half-life was determined to be 34.3 hours for $TNP_{LyP-1}$, demonstrating that the NPs enable dense loading and sustained release of the LXR agonist.

The release kinetics of GW3965 from the PS hybrid NPs showed a rapid release over the first 8 hours followed by a sustained release over 2 weeks. The drug release reached a maximum value over 14 days and the half-life was determined to be 72.9 hours, showing a delayed drug release compared to CNP with a half-life of 56.2 hours.

Example 5: Regulation of LXR Target Gene Expression by GW3965-Containing NPs In Vitro LXRs have shown beneficial effects in mouse models of atherosclerosis by regulating inflammation and lipid metabolism Calkin et al. *Arterioscler Thromb Vasc Biol* 30(8):1513-1518; Tangirala, et al. *Proc Natl Acad Sci USA* 99(18):11896-11901 (2002). LXRs directly control and regulate genes that may serve one of two biological functions: promote the efflux, catabolism or decreased absorption of cholesterol or facilitate the synthesis of fatty acids. In macrophages, LXRs seem to control transcription of several genes involved in the cholesterol efflux pathway, including ATP-binding cassette (ABC) A1, ABCG1, ABCG5 and ABCG8 Joseph and Tontonoz, *Curr Opin Pharmacol* 3(2): 192-197 (2003). Certain lipogenic genes such as SREBP-1c (sterol regulatory element binding protein) have also been identified as LXR targets Yoshikawa, et al. *Mol Cell Biol* 21(9):2991-3000 (2001). As a result, LXR ligands have been implicated to trigger induction of the lipogenic pathway in mice Joseph, et al. *J Biol Chem* 277(13):11019-11025 (2002); Schultz, et al. *Genes Dev* 14(22):2831-2838 (2000).

Experiments were conducted to assess the in vitro anti-inflammatory effects of GW3965-containing NPs and their ability to regulate LXR target gene expression such as ABCA1 and SREBP-1c. LPS-activated peritoneal macrophages were treated with the indicated NPs containing equivalent doses of GW3965. The supernatant was collected for ELISA analysis of MCP-1 and TNFα. The cells were collected for RT-qPCR analysis of MCP-1 and TNFα mRNA as described below.

Materials and Methods

In this study, ABCG1 and SREBP-1c were selected as target genes to examine the ability of GW3965-containing NPs to activate LXR in thioglycolate-elicited murine peritoneal macrophages. NPs containing equivalent dose of GW3965 were incubated with cells in the presence of growth media. The NP-mediated expression of both genes was determined 16 hours post-treatment by comparison of detected mRNA expression levels in treated groups against the untreated control. Data are presented as the fold difference in target gene expression normalized to GAPDH as the endogenous reference, and relative to the untreated control cells.

Anti-Inflammatory Effect of GW3965-Containing NPs In Vitro.

In the next set of experiments, GW3965-containing NPs were evaluated to see if they are able to exert anti-inflammatory effects on macrophages. Isolated murine peritoneal macrophages were first treated with lipopolysaccharide (LPS) to induce the production of pro-inflammatory factors such as MCP-1 and TNFα. The activated macrophages were then treated with an equivalent dose of GW3965 in either solution or NP form. ELISA assay was performed on the culture supernatant to determine the production of MCP-1 and TNFα.

Results

Treatment with LXR agonist substantially suppressed production of MCP-1 and TNFα proteins, which have been implicated in the pathogenesis of atherosclerosis. Further-more, when the LXR agonist was delivered within NPs, the production of both pro-inflammatory factors declined slightly compared to the drug-only counterpart. The cellular levels of pro-inflammatory genes, MCP-1 and TNFα, were also measured and a similar expression pattern in the LPS-activated murine peritoneal macrophages was observed. NPs either containing, or lacking, PS improved the anti-inflammatory effects of GW3965 by lowering cellular levels of MCP-1 gene compared to agonist only. Comparable suppression of TNFα expression was observed in activated macrophages treated by both NP formulations and LXR agonist only.

GW3965-containing NPs were significantly more effective than free agonist in inducing both ABCA1 and SREBP-1c expression in peritoneal macrophages. Notably, the incorporation of PS lipid within NPs further up-regulated expression of both LXR target genes. The hybrid NP that induced the highest gene expression was composed of a PLGA-b-PEG copolymer and PS lipid, with the polymer and lipid representing 90% and 10% of the NP mass, respectively. This result shows that it is possible to exploit LXR agonist-containing NPs to induce LXR target gene expression and promote cholesterol efflux from plaque macrophages.

Example 6: Targeting of Peptide-Functionalized NPs in Atherosclerotic Plaques In Vivo and Reduction in Plaque Size Col-IV is readily exposed in atherosclerotic lesions with compromised endothelial structural integrity. To determine whether Ac2-26 Col-IV NPs target to atherosclerotic lesions, experimental atherosclerosis was induced by feeding Ldlr−/− mice a W. type for 12 weeks. After 12 weeks, the diet was then switched to chow for an additional 3 weeks. During this time, Ac2-26 NPs or Ac2-26 Col-IV NPs each at 1 ug/mouse were i.v. injected 1×/week for 3 weeks. Aortic roots were then harvested, sectioned and assessed for NP targeting by confocal microcopy. Act-26 Col-IV NPs selectively targeted to lesions compared to Ac2-26 NPs.

In peritoneal macrophages, PS-NP treatment promoted the expression of LXR target genes and resulted in a substantial reduction of pro-inflammatory cytokines, MCP-1 and TNFα, when compared to the other NP formulations and free GW3695.

To determine their atheroprotective effects, the GW3965-containing nanoformulations were intravenously injected into low density lipoprotein receptor knockout (LDLr−/−) mice with diet-induced atherosclerotic plaques. An abundant accumulation of fluorescently labeled $TNP_{LyP-1}$ and $TNP_{CREKA}$ in the macrophage-rich plaques was observed. Short-term (14 days) treatment with $TNP_{LyP-1}$ and $TNP_{CREKA}$ reduced the lesion area by 17% and 16.5%, respectively, in LDLr−/− mice compared to untreated controls. These results demonstrate that these targeted NPs are useful for the treatment of atherosclerosis.

Materials and Methods

To detect homing of NPs to atherosclerotic plaques, the accumulation of intravenously injected CNP or TNT's that had been labeled with Alexa Fluor® 488 was investigated using the LDLr−/− mice model with induced atherosclerotic plaques. LDLr−/− mice were maintained on a western diet for 12 weeks to induce atherosclerotic plaques.

To explore the atheroprotective effects of these NPs, plaque-bearing LDLr−/− mice were randomly divided into five groups and treated with the following regimens with equivalent doses of 8 mg/kg entrapped GW3965 via daily intravenous administration for 14 consecutive days: i) empty PLGA-b-PEG NP without GW3965 (control); ii) GW3965 in solution form; iii) CNP; iv) $TNP_{LyP-1}$; and v) $TNP_{CREKA}$. The aim of this study was to determine whether GW3965-containing NPs would result in inhibition of atherosclerosis development and whether peptide conjugation would improve the delivery efficacy of GW3965.

Results

Fluorescence microscopy analysis of sectioned aortas which were excised 4 h after intravenous NP injection revealed enhanced accumulation of LyP-1 or CREKA (SEQ ID NO: 1) peptide functionalized NPs inside the plaque tissue when compared with CNP. In contrast, fewer fluorescently labeled CNPs (NPs formulated with PLGA-b-PEG) were observed in the plaques. Previous research has shown that LyP-1 specifically binds p32, a protein receptor that is highly expressed on plaque macrophages, which confers LyP-1 its homing specificity to macrophage-rich areas in atherosclerotic plaques.

Extensive accumulation of Alexa Fluor® 488 labeled $TNP_{LyP-1}$ was observed in areas positive for the CD68 macrophage marker, showing predominant colocalization of these TNPs within the macrophages. These results indicate that covalent attachment of LyP-1 or CREKA (SEQ ID NO: 1) peptides to PLGA-b-PEG NPs provides the ability to effectively deliver LXR agonists into atherosclerotic lesions.

All mice treated with GW 3965 in either solution or NP form exhibited a pronounced reduction in average lesion area for aortic sections when compared to control mice. Very strikingly, treatment with $TNP_{LyP-1}$ and $TNP_{CREKA}$ resulted in a statistically significant (p<0.001) decline in lesion area compared with CNPs, which is likely due to the marked accumulation of GW3965-containing $TNP_{LyP-1}$ and $TNP_{CREKA}$ within atherosclerotic lesions. Compared with controls, quantification of lesions after Oil Red O staining revealed a 17% reduction in lesion area for $TNP_{LyP-1}$ treatment, 16.5% for $TNP_{CREKA}$, and 6% for CNP, respectively. This provides strong evidence that $TNP_{LyP-1}$ and $TNP_{CREKA}$ mediated delivery of GW3965 exerts a greater atheroprotective effect compared to its non-targeted NP version.

In summary, two PLGA-b-PEG-based NP platforms were developed for targeted delivery of LXR agonist: i) polymer/PS hybrid NPs; and ii) LyP-1 or CREKA (SEQ ID NO: 1) peptide functionalized NPs. The versatile compositions of these NPs allow for effective encapsulation and sustained released of LXR agonist. The effects of these NPs on LXR target gene and inflammatory gene expression in vitro is significant. Enhanced accumulation of NPs within atherosclerotic plaques in LDLr−/− mice fed with a high-fat diet was achieved after peptide functionalization. Intravenous injection of GW3965-containing targeted NPs reduced the atherosclerotic lesions in LDLr−/− mice. These findings demonstrate that the NP platforms is optimized for efficient trafficking of LXR agonist.

We claim:

1. A method of promoting inflammation resolution by systemically or topically administering to the site of inflammation,
   biodegradable polymeric nanoparticles, wherein the diameter of the polymeric nanoparticles is less than 100 nms in diameter, comprising a mixture of amphiphilic polymer and/or hydrophobic polymer and/or lipid with amphiphilic polymer and/or hydrophobic polymer and/or lipid conjugated to targeting moieties that selectively bind to cells, tissues, or organs of the body at a site of inflammation associated with or resulting from a disease, disorder; trauma, chemotherapy or radiation,
   wherein the targeting moieties are present on the outer surface of the particles; and
   chemical or biologic inhibitor of inflammatory cytokines, their receptors, or their signaling molecules, or pro-inflammation resolving molecule selected from the group consisting of Ac2-26 and Resolvin D1, is encapsulated within the nanoparticles,
   wherein the targeting moiety and/or the chemical or biologic inhibitor of inflammatory cytokines or activators of inflammation resolving cytokines, their receptors, or their signaling molecules, or pro-inflammation resolving molecule, is conjugated to the amphiphilic or hydrophobic polymer by a linker which is hydrolysable by a chemical or enzymatic process present in elevated levels in areas of inflammation,
   wherein the chemical or biologic inhibitor of inflammatory cytokines, or activators of inflammation resolving cytokines, their receptors, or their signaling molecules, or pro-inflammation resolving molecule selected from the group consisting of Ac2-26 and Resolvin D1, is released from the particles after binding to the ligands at the site of inflammation, in an effective amount to resolve the inflammation.

2. The method of claim 1 wherein the inflammation to be resolved was caused by an inflammatory disease or disorder selected from the group consisting of cardiovascular disorders, ischemia, gastrointestinal disorders, chemotherapy of cancer, autoimmune diseases, traumatic central nervous system injury, hepatitis, nephritis, fibromyalgia, and reperfusion.

3. The method of claim 1 wherein the nanoparticles further comprise on the surface phosphatidyl serine incorporated into the nanoparticles in an effective amount to cause neutrophils to phagocytize the nanoparticles.

4. The method of claim 1 wherein the nanoparticles comprise targeting moieties that selectively bind inflamed cells or tissue conjugated to the amphiphilic or hydrophobic polymer by a linker which is hydrolysable by a chemical or enzymatic process present in elevated levels in areas of inflammation.

5. The method of claim 1 wherein the nanoparticles comprise chemical or biologic inhibitor of inflammatory cytokines, their receptors, or their signaling molecules or pro-inflammation resolving molecule selected from the group consisting of Ac2-26 and Resolvin D1 conjugated to the amphiphilic or hydrophobic polymer by a linker which is hydrolysable by a chemical or enzymatic process present in elevated levels in areas of inflammation.

6. The method of claim 1 wherein the nanoparticles comprise targeting moiety conjugated to polymer in a weight ratio of non-functionalized polymers of up to 39.

7. The method of claim 1 wherein the nanoparticles are administered to an individual with endotoxin-induced inflammation or individual with allergic inflammation, the nanoparticles comprising pro-inflammation resolving molecule Ac2-26 or Resolvin D1.

8. The method of claim 1 wherein the hydrophilic polymer is a polyethylene glycol copolymer or block copolymer.

9. The method of claim 1 wherein the nanoparticles are administered systemically.

10. The method of claim 1 wherein the nanoparticles are administered to a mucosal surface.

11. The method of claim 1 wherein the inflammatory disease or disorder is selected from the group consisting of cardiovascular disorders and reperfusion.

12. The method of claim 1 wherein the inflammation is caused by an autoimmune or inflammatory disease selected from the group consisting of dermatitis, diverticulitis, irritable bowel syndrome (IBS), systemic lupus erythematous (SLE), and obesity induced steatohepatitis.

13. The method of claim 1 wherein the nanoparticles comprise a targeting ligand LyP-I.

14. The method of claim 1 wherein the nanoparticles are administered to an ischemic tissue or reperfused tissue, the nanoparticles comprising pro-inflammation resolving molecule Ac2-26 or Resolvin D1.

15. The method of claim 1 wherein the hydrophilic polymer is polyethylene glycol.

16. The method of claim 1 wherein the nanoparticles are in a formulation comprising a pharmaceutically acceptable carrier for systemic administration by injection or infusion.

17. The method of claim 1 wherein the nanoparticles are in a formulation comprising a pharmaceutically acceptable carrier for topical or mucosal administration.

18. The method of claim 1 wherein the polymers forming the nanoparticles comprise linkers cleaved by hydrogen peroxide under the conditions present in neutrophils.

19. The method of claim 1, wherein the nanoparticles comprise a targeting ligand KLWVLPKGGGC (SEQ ID NO: 3).

20. The method of claim 1, wherein the nanoparticles further comprise an imaging agent.

* * * * *